US012626816B2

(12) United States Patent (10) Patent No.: US 12,626,816 B2
Witt                                                    (45) Date of Patent:      May 12, 2026

(54) SYSTEM, METHOD, AND COMPUTER PROGRAM PRODUCT FOR IDENTIFYING DEVICE CONNECTIONS

(71) Applicant: Becton, Dickinson and Company, Franklin Lakes, NJ (US)

(72) Inventor: Erik Kurt Witt, Oakland, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 18/603,449

(22) Filed: Mar. 13, 2024

(65) Prior Publication Data

US 2024/0221933 A1      Jul. 4, 2024

Related U.S. Application Data

(63) Continuation of application No. 18/115,411, filed on Feb. 28, 2023, now Pat. No. 11,967,423, which is a continuation of application No. 16/936,137, filed on Jul. 22, 2020, now Pat. No. 11,621,072, which is a continuation of application No. 16/382,361, filed on Apr. 12, 2019, now Pat. No. 10,762,991.

(60) Provisional application No. 62/659,863, filed on Apr. 19, 2018.

(51) Int. Cl.
   *G16H 40/63*      (2018.01)
   *A61M 5/168*      (2006.01)
   *G06F 13/14*      (2006.01)
   *G06F 13/38*      (2006.01)
   *G16H 10/60*      (2018.01)
   *H04L 61/4535*    (2022.01)

(52) U.S. Cl.
   CPC ........ *G16H 40/63* (2018.01); *A61M 5/16804* (2013.01); *G06F 13/14* (2013.01); *G06F 13/382* (2013.01); *G16H 10/60* (2018.01); *H04L 61/4535* (2022.05)

(58) Field of Classification Search
   CPC ... G16H 40/63; G16H 10/60; A61M 5/16804; G06F 13/14; G06F 13/382; H04L 61/1535
   See application file for complete search history.

(56)                References Cited

U.S. PATENT DOCUMENTS

| | | | |
|---|---|---|---|
| 6,985,870 | B2 | 1/2006 | Martucci et al. |
| 7,647,834 | B2 | 1/2010 | O'Mahony et al. |
| 7,782,202 | B2 | 8/2010 | Downie et al. |
| 7,811,279 | B2 | 10/2010 | John |
| 7,905,861 | B2 | 3/2011 | Rhinehart et al. |

(Continued)

FOREIGN PATENT DOCUMENTS

| | | |
|---|---|---|
| CN | 105163775 A | 12/2015 |
| CN | 106471193 A | 3/2017 |

(Continued)

*Primary Examiner* — Thomas D Alunkal
(74) *Attorney, Agent, or Firm* — The Webb Law Firm

(57)                ABSTRACT

A system, method, and computer program product for identifying device connections in a connection area includes receiving a plurality of physical parameters of a plurality of devices from a plurality of transmission sources in a connection area, wherein the plurality of physical parameters indicates physical states of the plurality of devices. At least one physical connection state is determined between the plurality of devices based on the plurality of physical parameters of the plurality of devices.

19 Claims, 15 Drawing Sheets

(56)                    References Cited

U.S. PATENT DOCUMENTS

| | | | |
|---|---|---|---|
| 7,976,508 | B2 | 7/2011 | Hoag |
| 8,330,579 | B2 | 12/2012 | Kneip et al. |
| 8,512,275 | B2 | 8/2013 | Childers et al. |
| 9,108,006 | B2 | 8/2015 | Jensen et al. |
| 9,138,516 | B2 | 9/2015 | Vischer et al. |
| 9,283,334 | B2 | 3/2016 | Mantell et al. |
| 9,452,256 | B2 | 9/2016 | Tieck et al. |
| 9,468,714 | B2 | 10/2016 | Butterfield et al. |
| 9,471,817 | B1 * | 10/2016 | Alhazme ............ G06K 19/0716 |
| 10,685,090 | B2 * | 6/2020 | Petterson ............... G16H 50/30 |
| 10,762,991 | B2 * | 9/2020 | Witt .................... H04L 61/4535 |
| 11,621,072 | B2 * | 4/2023 | Witt ........................ G16H 20/17 |
| | | | 340/5.24 |
| 11,967,423 | B2 * | 4/2024 | Witt .................. A61M 5/16804 |
| 2005/0277873 | A1 * | 12/2005 | Stewart ................. A61M 5/142 |
| | | | 604/93.01 |
| 2008/0058614 | A1 | 3/2008 | Banet et al. |
| 2009/0009290 | A1 * | 1/2009 | Kneip ................... A61M 1/155 |
| | | | 340/10.1 |
| 2009/0043253 | A1 | 2/2009 | Podaima |
| 2009/0079578 | A1 * | 3/2009 | Dvorsky ............ A61M 1/3656 |
| | | | 340/604 |
| 2010/0001838 | A1 | 1/2010 | Miodownik et al. |
| 2012/0075061 | A1 | 3/2012 | Barnes |
| 2012/0296279 | A1 | 11/2012 | Muller et al. |
| 2014/0088558 | A1 | 3/2014 | Holtwick et al. |
| 2015/0223732 | A1 | 8/2015 | Prince et al. |
| 2015/0352294 | A1 | 12/2015 | O'Mahony et al. |
| 2016/0015885 | A1 | 1/2016 | Pananen et al. |
| 2016/0089530 | A1 * | 3/2016 | Sathe ..................... A61M 39/20 |
| | | | 604/533 |
| 2016/0114104 | A1 | 4/2016 | Hyde et al. |
| 2017/0011240 | A1 | 1/2017 | Forster |
| 2019/0001057 | A1 * | 1/2019 | Tsoukalis ........... G06K 7/10366 |

FOREIGN PATENT DOCUMENTS

| | | |
|---|---|---|
| JP | H11154195 A | 6/1999 |
| JP | 2006126930 A | 5/2006 |
| JP | 2010524050 A | 7/2010 |
| JP | 2010204872 A | 9/2010 |
| JP | 5243548 A | 1/2011 |
| JP | 2014200415 A | 10/2014 |
| JP | 2017529942 A | 10/2017 |
| JP | 20185927 A | 1/2018 |
| JP | 2018500099 A | 1/2018 |
| WO | 2008097316 A1 | 8/2008 |
| WO | 2009055733 A | 4/2009 |
| WO | 2012040248 A2 | 3/2012 |

* cited by examiner

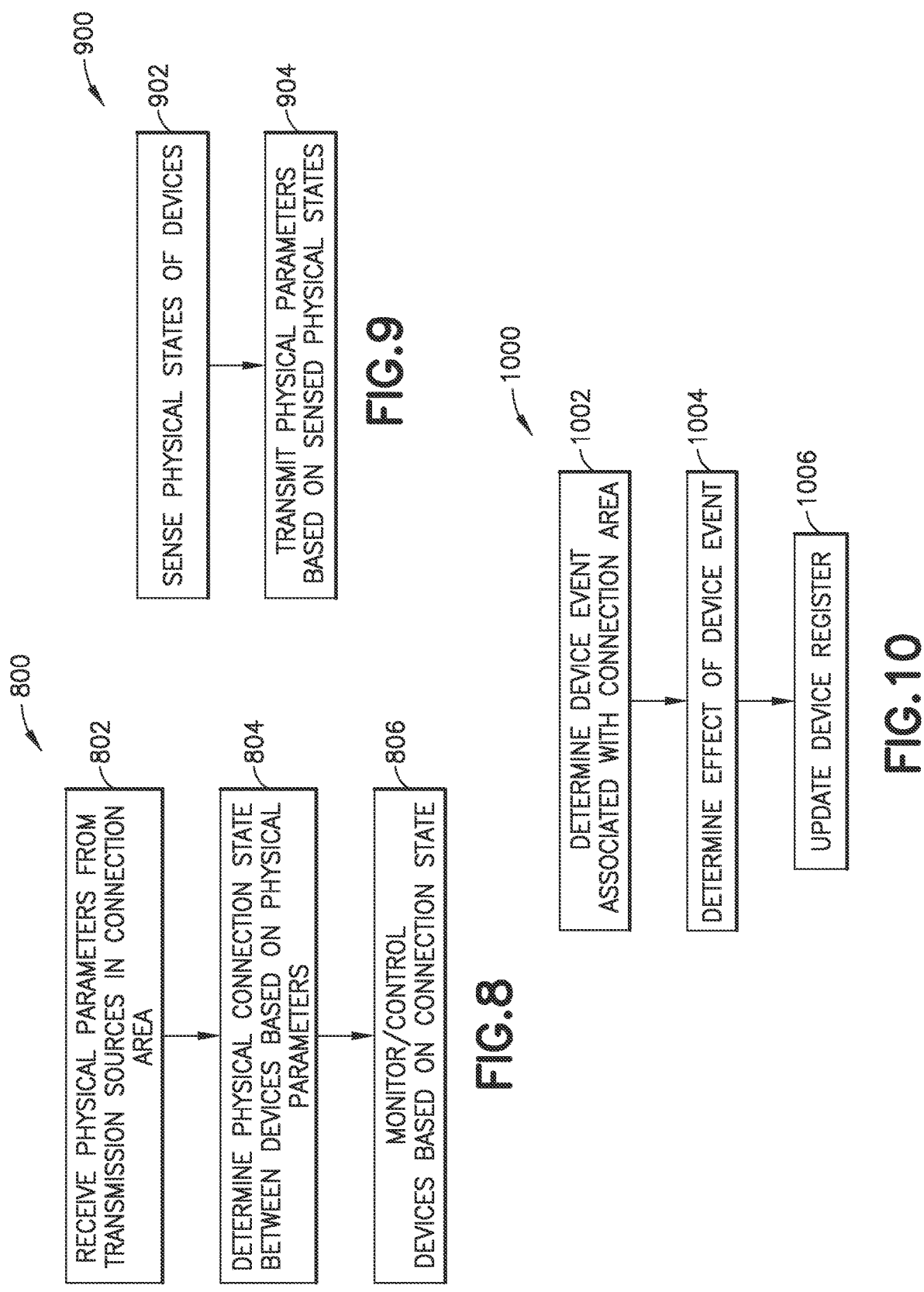

900

902 SENSE PHYSICAL STATES OF DEVICES

904 TRANSMIT PHYSICAL PARAMETERS BASED ON SENSED PHYSICAL STATES

1002 DETERMINE DEVICE EVENT ASSOCIATED WITH CONNECTION AREA

1004 DETERMINE EFFECT OF DEVICE EVENT

1006 UPDATE DEVICE REGISTER

802 RECEIVE PHYSICAL PARAMETERS FROM TRANSMISSION SOURCES IN CONNECTION AREA

804 DETERMINE PHYSICAL CONNECTION STATE BETWEEN DEVICES BASED ON PHYSICAL PARAMETERS

806 MONITOR/CONTROL DEVICES BASED ON CONNECTION STATE

EXAMPLE DATA STREAM FROM RECEIVER

| TIME INDEX | 01–ID | 01–ACTIVE | 02–ID | 02–ACTIVE | 03–ID | 03–ACTIVE | 04–ID | 04–ACTIVE | 05–ID | 05–ACTIVE | 06–ID | 06–ACTIVE | COINCIDENCE LOGIC | DESCRIPTION |
|---|---|---|---|---|---|---|---|---|---|---|---|---|---|---|
| 2035 | | | | | | | | | | | | | | NO DEVICES IN FIELD |
| 2036 | 189 | 0 | 188 | 0 | | | | | | | | | | CATHETER IN FIELD |
| 2037 | 189 | 0 | 188 | 0 | | | | | | | | | | |
| 2038 | 189 | 1 | 188 | 0 | | | | | | | | | | CATHETER PLACED (DEPLOYED) |
| 2039 | 189 | 1 | 188 | 0 | | | | | | | | | | |
| 2040 | 189 | 1 | 188 | 0 | 144 | 0 | 143 | 0 | | | | | | IV SET IN FIELD |
| 2041 | 189 | 1 | 188 | 1 | 144 | 1 | 143 | 0 | | | | | 188+144 | IV SET CONNECTED TO CATHETER |
| 2042 | 189 | 1 | 188 | 1 | 144 | 1 | 143 | 0 | | | | | | |
| 2043 | 189 | 1 | 188 | 1 | 144 | 1 | 143 | 0 | | | | | | |
| 2044 | 189 | 1 | 188 | 1 | 144 | 1 | 143 | 0 | | | | | | |
| 2045 | 189 | 1 | 188 | 1 | 144 | 1 | 143 | 0 | | | | | | |
| 2046 | 189 | 1 | 188 | 1 | 144 | 1 | 143 | 0 | 164 | 0 | | | | FIRST DRUG SYRINGE IN FIELD |
| 2047 | 189 | 1 | 188 | 1 | 144 | 1 | 143 | 0 | 164 | 0 | | | | |
| 2048 | 189 | 1 | 188 | 1 | 144 | 1 | 143 | 1 | 164 | 1 | | | 143+164 | FIRST DRUG SYRINGE CONNECTED TO IV SET |
| 2049 | 189 | 1 | 188 | 1 | 144 | 1 | 143 | 1 | 164 | 1 | | | | |
| 2050 | 189 | 1 | 188 | 1 | 144 | 1 | 143 | 1 | 164 | 1 | | | | |
| 2051 | 189 | 1 | 188 | 1 | 144 | 1 | 143 | 1 | 164 | 0 | | | 143–164 | FIRST SYRINGE DISCONNECTED FROM IV SET |
| 2052 | 189 | 1 | 188 | 1 | 144 | 1 | 143 | 1 | 164 | 0 | | | | |
| 2053 | 189 | 1 | 188 | 1 | 144 | 1 | 143 | 1 | 193 | 0 | | | | FIRST DRUG SYRINGE LEAVES FIELD |
| 2054 | 189 | 1 | 188 | 1 | 144 | 1 | 143 | 1 | 193 | 0 | | | | |
| 2055 | 189 | 1 | 188 | 1 | 144 | 1 | 143 | 1 | 193 | 0 | | | | SECOND DRUG SYRINGE ENTERS FIELD |
| 2056 | 189 | 1 | 188 | 1 | 144 | 1 | 143 | 1 | 193 | 0 | | | | |
| 2057 | 189 | 1 | 188 | 1 | 144 | 1 | 143 | 1 | 193 | 0 | | | | |
| 2058 | 189 | 1 | 188 | 1 | 144 | 1 | 143 | 1 | 193 | 0 | 120 | 0 | | FLUSH SYRINGE ENTERS FIELD |
| 2059 | 189 | 1 | 188 | 1 | 144 | 1 | 143 | 1 | 193 | 0 | 120 | 0 | | |
| 2060 | 189 | 1 | 188 | 1 | 144 | 1 | 143 | 1 | 193 | 1 | 120 | 1 | 143+120 | FLUSH SYRINGE CONNECTED TO IV SET |
| 2061 | 189 | 1 | 188 | 1 | 144 | 1 | 143 | 1 | 193 | 1 | 120 | 1 | | |
| 2062 | 189 | 1 | 188 | 1 | 144 | 1 | 143 | 1 | 193 | 0 | 120 | 0 | 143–120 | FLUSH SYRINGE DISCONNECTED FROM IV SET |

DEVICE REGISTER

SYSTEM, METHOD, AND COMPUTER PROGRAM PRODUCT FOR IDENTIFYING DEVICE CONNECTIONS

CROSS-REFERENCE TO RELATED APPLICATION

The present application is a continuation application of U.S. patent application Ser. No. 18/115,411 entitled "System, Method, and Computer Program Product for Identifying Device Connections", filed Feb. 28, 2023, which is a continuation application of U.S. patent application Ser. No. 16/936,137 entitled "System, Method, and Computer Program Product for Identifying Device Connections", filed Jul. 22, 2020 (now U.S. Pat. No. 11,621,072), which is a continuation application of U.S. patent application Ser. No. 16/382,361, entitled "System, Method, and Computer Program Product for Identifying Device Connections", filed Apr. 12, 2019 (now U.S. Pat. No. 10,762,991), which claims priority to U.S. Provisional Application Ser. No. 62/659,863, entitled "System, Method, and Computer Program Product for Identifying Device Connections", filed Apr. 19, 2018, the entire disclosures of each of which are hereby incorporated by reference in their entirety.

BACKGROUND

1. Field

The present disclosure relates generally to identifying devices and, in some non-limiting embodiments or aspects, to a system, method, and computer program product for identifying devices that are being or have been connected and/or identifying connections between devices.

2. Technical Considerations

In certain applications, it is important to determine when two devices are connected with each other. This is a relatively straightforward problem if devices to be connected are able to directly interact with each other. For example, in a case of an electrical connection between two devices, establishment of a current flow can indicate a presence of a connection between the two devices, e.g., one of the mating connectors may complete a circuit in its complement.

Hospitals have conventionally used Bar Code Medication Administration (BCMA) systems to reduce medication error. BCMA systems include a handheld barcode reader, which includes an integrated processor and a wireless connection. A computer server with software is integrated with other hospital IT systems, (e.g., an electronic medication administration record), to verify that an identified patient is the intended recipient of a medicine in a container. In use, prior to administering a medication to a patient, a nurse scans a wristband barcode on the patient, and scans a barcode on the container to verify that the medication in the container is the correct medication for the patient. In some implementations, the nurse may also scan his or her own badge barcode. BCMA systems require the use of a handheld electronic device that is inconvenient, requires manual management, and is a contamination risk.

Further, although BCMA systems can help confirm the five "rights" of medication administration: right patient, right drug, right dose, right route, and right time, and reduce medication administration errors, many workarounds to BCMA systems exist, such as affixing patient identification barcodes to computer carts, scanners, doorjambs, or nurses' belt rings, carrying several patients' pre-scanned medications on carts, and the like. Nurses or other medical professionals may override and/or ignore BCMA alerts and/or procedures for various reasons. For example, some causes of these workarounds include unreadable medication barcodes (e.g., barcodes that are crinkled, smudged, torn, missing, and/or covered by another label), malfunctioning scanners, unreadable or missing patient identification wristbands (e.g., wristbands that are chewed, soaked, and/or missing), non-barcoded medications, failing batteries, uncertain wireless connectivity, emergencies, and the like. Possible consequences of workarounds include incorrect administration of medications, incorrect doses, incorrect medication administration times, and incorrect medication formulations, and the like. Shortcomings in BCMA system design, implementation, and workflow integration may encourage these workarounds. Moreover, integrating BCMA systems within real-world clinical workflows requires attention to in situ use to ensure correct use of safety features of BCMA systems.

U.S. Pat. No. 7,782,202 discloses a system for identifying a connection of two or more components in which one or more RFID transponders are associated with the two or more components. However, U.S. Pat. No. 7,782,202 requires using an electrical connection between devices to determine connection of a particular plug and a particular socket on a pairwise basis. Moreover, U.S. Pat. No. 7,782,202 does not disclose detection of a connection event, only determination that a connection between devices exists.

U.S. Pat. No. 7,976,508 is directed to a medication safety system that includes a panel mounted to an IV pole above a multi-channel infusion pump also mounted to the IV pole. However, the panel requires an RFID reader for each channel of the multi-channel infusion pump for reading the RFID tags placed on each of the medication containers mounted to the panel, not RFID transmitters on each of the channels and the medication containers.

Therefore, there is a need in the art for connection identification systems and methods that enable use of independent connection sensors that are sealed from the environment, create a simplified workflow for caregivers, reduce a need and possibility for workarounds, eliminate hand-held scanners as vectors of infection, provide increased detail regarding route of administration, monitor of all points of entry that can result in fluid being delivered to a patient, and/or achieve higher reliability and specificity of radio detection.

SUMMARY

Accordingly, it is an object of the present disclosure to provide a method, system, and computer program product for identifying device connections that overcomes some or all of the deficiencies of the prior art.

According to a non-limiting embodiment or aspect, provided is a system for identifying device connections in a connection area, comprising at least one computer including at least one processor, the at least computer programmed and/or configured to: receive a plurality of physical parameters of a plurality of devices from a plurality of transmission sources in a connection area, wherein the plurality of physical parameters indicates physical states of the plurality of devices; and determine at least one physical connection state between the plurality of devices based on the plurality of physical parameters of the plurality of devices.

According to a non-limiting embodiment or aspect, provided is a system for identifying device connections in a connection area comprising: at least one first device; at least one second device, wherein the at least one first device is configured to be physically connected to the at least one second device; at least one first sensor on the at least one first device, wherein the at least one first sensor is configured to sense at least one physical state of the at least one first device to determine at least one first physical parameter of the at least one first device; at least one first transmission source on the at least one first device, wherein the at least one first transmission source is configured to transmit the at least one first physical parameter of the at least one first device; at least one second sensor on the at least one second device, wherein the at least one second sensor is configured to sense at least one physical state of the at least one second device to determine at least one second physical parameter of the at least one second device; at least one second transmission source on the at least one second device, wherein the at least one second transmission source is configured to transmit the at least one second physical parameter of the at least one second device; at least one receiver configured to detect the at least one first transmission source in a connection area, detect the at least one second transmission source in the connection area, receive the at least one first physical parameter from the at least one first transmission source, and receive the at least one second physical parameter from the at least one second transmission source.

According to a non-limiting embodiment or aspect, provided is a computer-implemented method for identifying device connections in a connection area, the method comprising: receiving, with at least one processor, a plurality of physical parameters of a plurality of devices from a plurality of transmission sources in a connection area, wherein the plurality of physical parameters indicates physical states of the plurality of devices; and determining, with at least one processor, at least one physical connection state between the plurality of devices based on the plurality of physical parameters of the plurality of devices.

According to a non-limiting embodiment or aspect, provided is a method for identifying device connections in a connection area comprising: sensing, with at least one first sensor on at least one first device, at least one physical state of the at least one first device to determine at least one first physical parameter of the at least one first device; transmitting, with at least one first transmission source on the at least one first device, the at least one first physical parameter of the at least one first device; sensing, with at least one second sensor on at least one second device, at least one physical state of the at least one second device to determine at least one second physical parameter of the at least one second device; transmitting, with at least one second transmission source on the at least one second device, the at least one second physical parameter of the at least one second device; with at least one signal receiver, detecting the at least one first transmission source in a connection area, detecting the at least one second transmission source in the connection area, receiving the at least one the at least one first physical parameter from the at least one first transmission source, and receiving the at least one second physical parameter from the at least one second transmission source.

It is noted herein that a multitude of receivers may be included in the system. Each receiver may have a reception area that depends on many factors, including objects blocking and/or reflecting radio signals. Accordingly, which specific receiver picks up signals from each device can be variable. Signals from devices undergoing connections may be detected by different receivers. In one configuration, an individual transmitter can be received by multiple receivers. In another configuration, each transmitter of a pair of devices can be detected by different receivers. In yet another configuration, pairs of device transmitters can be detected by multiple receivers. Combinatorial logic can determine from complex and potentially redundant data received from multiple receivers which transmitters have been connected together.

According to a non-limiting embodiment or aspect, provided is a computer program product for dynamic application selection for electronic medical records, the computer program product comprising at least one non-transitory computer-readable medium including program instructions that, when executed by at least one processor cause the at least one processor to: receive a plurality of physical parameters of a plurality of devices from a plurality of transmission sources in a connection area, wherein the plurality of physical parameters indicates physical states of the plurality of devices; and determine at least one physical connection state between the plurality of devices based on the plurality of physical parameters of the plurality of devices.

Further embodiments or aspects are set forth in the following numbered clauses:

Clause 1. A system for identifying device connections in a connection area, comprising at least one computer including at least one processor, the at least computer programmed and/or configured to: receive a plurality of physical parameters of a plurality of devices from a plurality of transmission sources in a connection area, wherein the plurality of physical parameters indicates physical states of the plurality of devices; and determine at least one physical connection state between the plurality of devices based on the plurality of physical parameters of the plurality of devices.

Clause 2. The system of clause 1, wherein the at least one computer is programmed and/or configured to control a flow of a fluid in a fluid flow path including at least one device of the plurality of devices based on the at least one physical connection state between the plurality of devices.

Clause 3. The system of clause 1 or 2, wherein the at least one computer is programmed and/or configured to: receive a patient identifier associated with a patient; receive a medication identifier of a medication to be delivered to the patient via the fluid flow path; associate the patient identifier and the medication identifier with the at least one device of the fluid flow path; and control the flow of the fluid in the fluid flow path based on the patient identifier and the medication identifier.

Clause 4. The system of any of clauses 1-3, wherein the at least one computer is programmed and/or configured to: generate a digital representation of a fluid flow path including at least one device of the plurality of devices based on the at least one physical connection state between the plurality of devices; and monitor a flow of a fluid in the fluid flow path based on the representation of the fluid flow path.

Clause 5. The system of any of clauses 1-4, wherein the at least one computer is programmed and/or configured to output or cause the output of an audible and/or visible indication in the connection area, wherein the audible and/or visible indication indicates a status of the fluid flow path.

Clause 6. The system of any of clauses 1-5, wherein the plurality of physical parameters is associated with a plurality of event times, wherein the plurality of event times indicates times of changes in the physical states of the plurality of devices, and wherein the at least one computer is programmed and/or configured to determine the at least one connection state based on the plurality of event times.

Clause 7. The system of any of clauses 1-6, wherein the at least one computer is programmed and/or configured to determine whether the plurality of event times are within a sliding time window.

Clause 8. The system of any of clauses 1-7, wherein the at least one computer is programmed and/or configured to: determine that at least one device of the plurality of devices is within the connection area, the at least one device associated with at least one physical parameter of the plurality of physical parameters; receive a device identifier associated with the at least one device; associate the device identifier with the at least one physical parameter of the at least one device; and update a device register including a list of devices in the connection area with the device identifier in association with the at least one physical parameter.

Clause 9. The system of any of clauses 1-8, wherein the at least one computer is programmed and/or configured to: determine that the at least one device is outside the connection area; and remove the device identifier from the device register.

Clause 10. The system of any of clauses 1-9, wherein the at least one computer is programmed and/or configured to determine the at least one connection state between the plurality of devices based on at least one predefined compatibility of the plurality of devices.

Clause 11. The system of any of clauses 1-10, wherein the plurality of physical parameters indicate a plurality of different physical states of the plurality of devices.

Clause 12. The system of any of clauses 1-11, wherein at least one physical parameter of the plurality of physical parameters indicates a finite set of states of a physical state of at least one device of the plurality of devices.

Clause 13. The system of any of clauses 1-12, wherein at least one physical parameter of the plurality of physical parameters indicates a magnitude of change in a physical state of at least one device of the plurality of devices.

Clause 14. The system of any of clauses 1-13, wherein at least one physical parameter of the plurality of physical parameters includes a plurality of connection parameters that indicates physical states of a plurality of connectors of at least one device of the plurality of devices, and wherein the at least one physical connection state is determined based on at least one connection parameter of at least one connector of the at least one device.

Clause 15. The system of any of clause 1-14, further comprising: the plurality of devices; a plurality of sensors on the plurality of devices, wherein the plurality of sensors are configured to sense the physical states of the plurality of devices to determine the plurality of physical parameters; the plurality of transmission sources on the plurality of devices, wherein the plurality of transmission sources are configured to transmit the plurality of physical parameters; at least one receiver configured to detect the plurality of transmission sources in the connection area, receive the plurality of physical parameters from the plurality of transmission sources, and provide the plurality of physical parameters to the at least one computer including at least one processor.

Clause 16. The system of any of clauses 1-15, wherein the at least one receiver comprises the at least one computer including at least one processor.

Clause 17. The system of any of clauses 1-16, wherein the at least one computer including at least one processor is remote from the at least one receiver.

Clause 18. The system of any of clauses 1-17, wherein the at least one receiver comprises a plurality of receivers in the connection area, and wherein the plurality of receivers are configured to communicate with the at least one remote computer.

Clause 19. The system of any of clauses 1-18, wherein the at least one remote computer is programmed and/or configured to: receive a second plurality of physical parameters of a second plurality of devices from a second plurality of transmission sources in a second connection area outside the first connection area, wherein the second plurality of physical parameters indicates physical states of the second plurality of devices; and determine at least one second physical connection state between the second plurality of devices based on the second plurality of physical parameters of the second plurality of devices.

Clause 20. A system for identifying device connections in a connection area comprising: at least one first device; at least one second device, wherein the at least one first device is configured to be physically connected to the at least one second device; at least one first sensor on the at least one first device, wherein the at least one first sensor is configured to sense at least one physical state of the at least one first device to determine at least one first physical parameter of the at least one first device; at least one first transmission source on the at least one first device, wherein the at least one first transmission source is configured to transmit the at least one first physical parameter of the at least one first device; at least one second sensor on the at least one second device, wherein the at least one second sensor is configured to sense at least one physical state of the at least one second device to determine at least one second physical parameter of the at least one second device; at least one second transmission source on the at least one second device, wherein the at least one second transmission source is configured to transmit the at least one second physical parameter of the at least one second device; at least one receiver configured to detect the at least one first transmission source in a connection area, detect the at least one second transmission source in the connection area, receive the at least one first physical parameter from the at least one first transmission source, and receive the at least one second physical parameter from the at least one second transmission source.

Clause 21. The system of clause 20, wherein the at least one first device comprises a plurality of connectors configured to be physically connected to at least one of the following: a patient, the at least one second device, at least one third device, one or more connectors of the at least one second device, one or more connectors of the at least one third device, or any combination thereof, and wherein the at least one first physical parameter includes a plurality of connection parameters that indicates physical states of the plurality of connectors of the at least one first device.

Clause 22. The system of clause 20 or 21, wherein the at least one first physical parameter includes information that indicates at least one predetermined connection state between two or more connectors of the plurality of connectors of the at least one first device.

Clause 23. The system of any of clauses 20-22, further comprising: at least one computer including at least one processor, the at least computer programmed and/or configured to: receive at least one first event time associated with the at least one first device physical parameter; receive at least one second event time associated with the at least one second device physical parameter; and determine at least one connection state between the at least one first device and the at least one second device based on the at least one first device physical parameter, the at least one second device physical parameter, the at least one first event time, and the at least one second event time.

Clause 24. The system of any of clauses 20-23, wherein the at least one first devices comprises one of the following: a syringe, an IV spike, an IV access site, an IV bag, an IV set, a catheter, a medical device connector, or any combination thereof.

Clause 25. The system of any of clauses 20-24, wherein the at least one first transmission source comprises an RFID transmission source.

Clause 26. The system of any of clauses 20-25, wherein the at least one first sensor comprises a pressure sensor.

Clause 27. The system of any of clauses 20-26, further comprising: at least one tag including the at least one first sensor and the at least one first transmission source are integrally formed with the at least one tag, wherein the at least one first sensor and the at least one first transmission source are sealed from an environment outside the at least one tag.

Clause 28. The system of any of clauses 20-27, wherein the at least one tag is ring shaped.

Clause 29. The system of any of clauses 20-28, wherein the at least one first device forms at least a portion of a fluid flow path, and wherein the at least one tag is attached to the at least one first device at a fluid outlet or a fluid inlet of the at least one first device.

Clause 30. The system of any of clauses 20-29, wherein the at least one receiver comprises a plurality of receivers spaced apart from one another in the connection area.

Clause 30a. The system of clause 1, wherein the identity of the plurality of devices is a capping or decapping event.

Clause 30b. The system of clause 1, wherein the identity of the plurality of devices is a monitoring of placement of a component into or out of the system event.

Clause 30c. The system of clause 30, wherein the monitoring of placement of a component is monitoring placement of a catheter securement device.

Clause 30d. The system of clause 1, wherein the identity of the plurality of devices is a disinfection state of at least one component of the system.

Clause 30e. The system of clause 30d, wherein the disinfection of at least one component of the system event is a preparation of an IV site with an antimicrobial agent.

Clause 31. A computer-implemented method for identifying device connections in a connection area, the method comprising: receiving, with at least one processor, a plurality of physical parameters of a plurality of devices from a plurality of transmission sources in a connection area, wherein the plurality of physical parameters indicates physical states of the plurality of devices; and determining, with at least one processor, at least one physical connection state between the plurality of devices based on the plurality of physical parameters of the plurality of devices.

Clause 32. The method of clause 31, further comprising: controlling, with at least one processor, a flow of a fluid in a fluid flow path including at least one device of the plurality of devices based on the at least one physical connection state between the plurality of devices.

Clause 33. The method of clause 31 or 32, further comprising: receiving, with at least one processor, a patient identifier associated with a patient; receiving, with at least one processor, a medication identifier of a medication to be delivered to the patient via the fluid flow path; associating, with at least one processor, the patient identifier and the medication identifier with the at least one device of the fluid flow path; and controlling, with at least one processor, the flow of the fluid in the fluid flow path based on the patient identifier and the medication identifier.

Clause 34. The method of any of clauses 31-33, further comprising: generating, with at least one processor, a digital representation of a fluid flow path including at least one device of the plurality of devices based on the at least one physical connection state between the plurality of devices; and monitoring, with at least one processor, a flow of a fluid in the fluid flow path based on the representation of the fluid flow path.

Clause 35. The method of any of clauses 31-34, further comprising: controlling, with at least one processor, an audio and/or visual output device to output an audible and/or visible indication in the connection area, wherein the audible and/or visible indication indicates a status of the fluid flow path.

Clause 36. The method of any of clauses 31-35, wherein the plurality of physical parameters is associated with a plurality of event times, wherein the plurality of event times indicates times of changes in the physical states of the plurality of devices, the method further comprising: determining, with at least one processor, the at least one connection state based on the plurality of event times.

Clause 37. The method of any of clauses 31-36, further comprising: determining, with at least one processor, whether the plurality of event times are within a sliding time window.

Clause 38. The method of any of clauses 31-37, further comprising: determining, with at least one processor, that at least one device of the plurality of devices is within the connection area, the at least one device associated with at least one physical parameter of the plurality of physical parameters; receiving, with at least one processor, a device identifier associated with the at least one device; associating, with at least one processor, the device identifier with the at least one physical parameter of the at least one device; and updating, with at least one processor, a device register including a list of devices in the connection area with the device identifier in association with the at least one physical parameter.

Clause 39. The method of any of clauses 31-38, further comprising: determining, with at least one processor, that the at least one device is outside the connection area; and removing, with at least one processor, the device identifier from the device register.

Clause 40. The method of any of clauses 31-39, further comprising: determining, with at least one processor, the at least one connection state between the plurality of devices based on at least one predefined compatibility of the plurality of devices.

Clause 41. The method of any of clauses 31-40, wherein the plurality of physical parameters indicate a plurality of different physical states of the plurality of devices.

Clause 42. The method of any of clauses 31-41, wherein at least one physical parameter of the plurality of physical parameters indicates a finite set of states of a physical state of at least one device of the plurality of devices.

Clause 43. The method of any of clauses 31-42, wherein at least one physical parameter of the plurality of physical parameters indicates a magnitude of change in a physical state of at least one device of the plurality of devices.

Clause 44. The method of any of clauses 31-43, wherein at least one physical parameter of the plurality of physical parameters includes a plurality of connection parameters that indicates physical states of a plurality of connectors of at least one device of the plurality of devices, and wherein the at least one physical connection state is determined based on at least one connection parameter of at least one connector of the at least one device.

Clause 45. The method of any of clauses 31-44, further comprising: sensing, with a plurality of sensors on the plurality of devices, the physical states of the plurality of devices to determine the plurality of physical parameters; transmitting, with a plurality of transmission sources on the plurality of devices, the plurality of physical parameters; and with at least one receiver, detecting the plurality of transmission sources in the connection area, receiving the plurality of physical parameters from the plurality of transmission sources.

Clause 46. The method of any of clauses 31-45, further comprising: transmitting, with at least one receiver, the plurality of physical parameters to at least one remote computer including at least one processor.

Clause 47. The method of any of clauses 31-46, further comprising: with at least one remote computer, receiving the plurality of physical parameters, receiving a second plurality of physical parameters of a second plurality of devices from a second plurality of transmission sources in a second connection area outside the first connection area, wherein the second plurality of physical parameters indicates physical states of the second plurality of devices, and determining at least one second physical connection state between the second plurality of devices based on the second plurality of physical parameters of the second plurality of devices.

Clause 48. A method for identifying device connections in a connection area comprising: sensing, with at least one first sensor on at least one first device, at least one physical state of the at least one first device to determine at least one first physical parameter of the at least one first device; transmitting, with at least one first transmission source on the at least one first device, the at least one first physical parameter of the at least one first device; sensing, with at least one second sensor on at least one second device, at least one physical state of the at least one second device to determine at least one second physical parameter of the at least one second device; transmitting, with at least one second transmission source on the at least one second device, the at least one second physical parameter of the at least one second device; with at least one signal receiver, detecting the at least one first transmission source in a connection area, detecting the at least one second transmission source in the connection area, receiving the at least one at the at least one first physical parameter from the at least one first transmission source, and receiving the at least one second physical parameter from the at least one second transmission source.

Clause 49. The method of clause 48, wherein the at least one first device comprises a plurality of connectors configured to be physically connected to at least one of the following: a patient, the at least one second device, at least one third device, one or more connectors of the at least one second device, one or more connectors of the at least one third device, or any combination thereof, and wherein the at least one first physical parameter includes a plurality of connection parameters that indicates physical states of the plurality of connectors of the at least one first device.

Clause 50. The method of clause 48 or 49, wherein the at least one first physical parameter includes information that indicates at least one predetermined connection state between two or more connectors of the plurality of connectors of the at least one first device.

Clause 51. The method of any of clauses 48-50, further comprising: receiving, with at least one processor, at least one first event time associated with the at least one first device physical parameter; receiving, with at least one processor, at least one second event time associated with the at least one second device physical parameter; and determining, with at least one processor, at least one connection state between the at least one first device and the at least one second device based on the at least one first device physical parameter, the at least one second device physical parameter, the at least one first event time, and the at least one second event time.

Clause 52. The method of any of clauses 48-51, wherein the at least one first devices comprises one of the following: a syringe, an IV spike, an IV access site, an IV bag, an IV set, a catheter, a medical device connector, or any combination thereof.

Clause 53. The method of any of clauses 48-52, wherein the at least one first transmission source comprises a wireless transmission source.

Clause 54. The method of any of clauses 48-53, wherein the at least one first sensor comprises a pressure sensor. Optionally, the pressure sensor can be a momentary switch, which operates to output a binary output if pressure exceeds a specified threshold.

Clause 55. The method of any of clauses 48-54, wherein the at least one first transmission source transmits the at least one first physical parameter in response entering the connection area.

Clause 56. The method of any of clauses 48-55, wherein the at least one first transmission source transmits the at least one first physical parameter in response to the at least one first sensor sensing a change in the at least one physical state of the at least one first device.

Clause 57. A computer program product for dynamic application selection for electronic medical records, the computer program product comprising at least one non-transitory computer-readable medium including program instructions that, when executed by at least one processor cause the at least one processor to: receive a plurality of physical parameters of a plurality of devices from a plurality of transmission sources in a connection area, wherein the plurality of physical parameters indicates physical states of the plurality of devices; and determine at least one physical connection state between the plurality of devices based on the plurality of physical parameters of the plurality of devices.

It is appreciated herein that the transmitter may send information about the activation state or connection state of a device being used. Along with these states, a device identity may be conveyed, which can either be unique (for example, at the SKU level), or general device-type. Individual unique device identity can be used to identify the SKU, which can be used to identify the type of device.

It is further appreciated herein that the system can include a database of devices that contain a digital description of the physical characteristics of a device being used at a facility. This database may contain, for example, the fluid path structure of each device, allowed interactions between devices, inlets and outlets, connection points, and fluid path lengths and volumes between them. For example, an IV set could be detected. A digital representation could contain the position of connectors and the structure of the branching fluid path between all inlets and outlets.

It is further appreciated herein that the system can include a database which can be accessed by the computer application to create a digital representation of the fluid path, interactions of the devices within the fluid path, and other devices in the receiver area.

It is still further contemplated that the system can include a computer application which uses information in the database to resolve conflicts. For example, if two sets of connections are detected simultaneously, information in the database can help resolve which pairs of connections have the highest likelihood of being correct.

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the present disclosure. As used in the specification and the claims, the singular form of "a," "an," and "the" include plural referents unless the context clearly dictates otherwise.

BRIEF DESCRIPTION OF THE DRAWINGS

Additional advantages and details of embodiments or aspects of the present disclosure are explained in greater detail below with reference to the exemplary embodiments that are illustrated in the accompanying schematic figures, in which:

FIG. 8 is a flowchart of a non-limiting embodiment or aspect of a process for identifying device connections in a connection area according to embodiments or aspects of the present disclosure;

FIG. 9 is another flowchart of a non-limiting embodiment or aspect of a process for identifying device connections in a connection area according to embodiments or aspects of the present disclosure;

FIG. 10 is another flowchart of a non-limiting embodiment or aspect of a process for identifying device connections in a connection area according to embodiments or aspects of the present disclosure;

FIG. 11C is a table of example data of an implementation of a non-limiting embodiment or aspect of processes shown in FIGS. 8-10;

DETAILED DESCRIPTION

Figure 1:
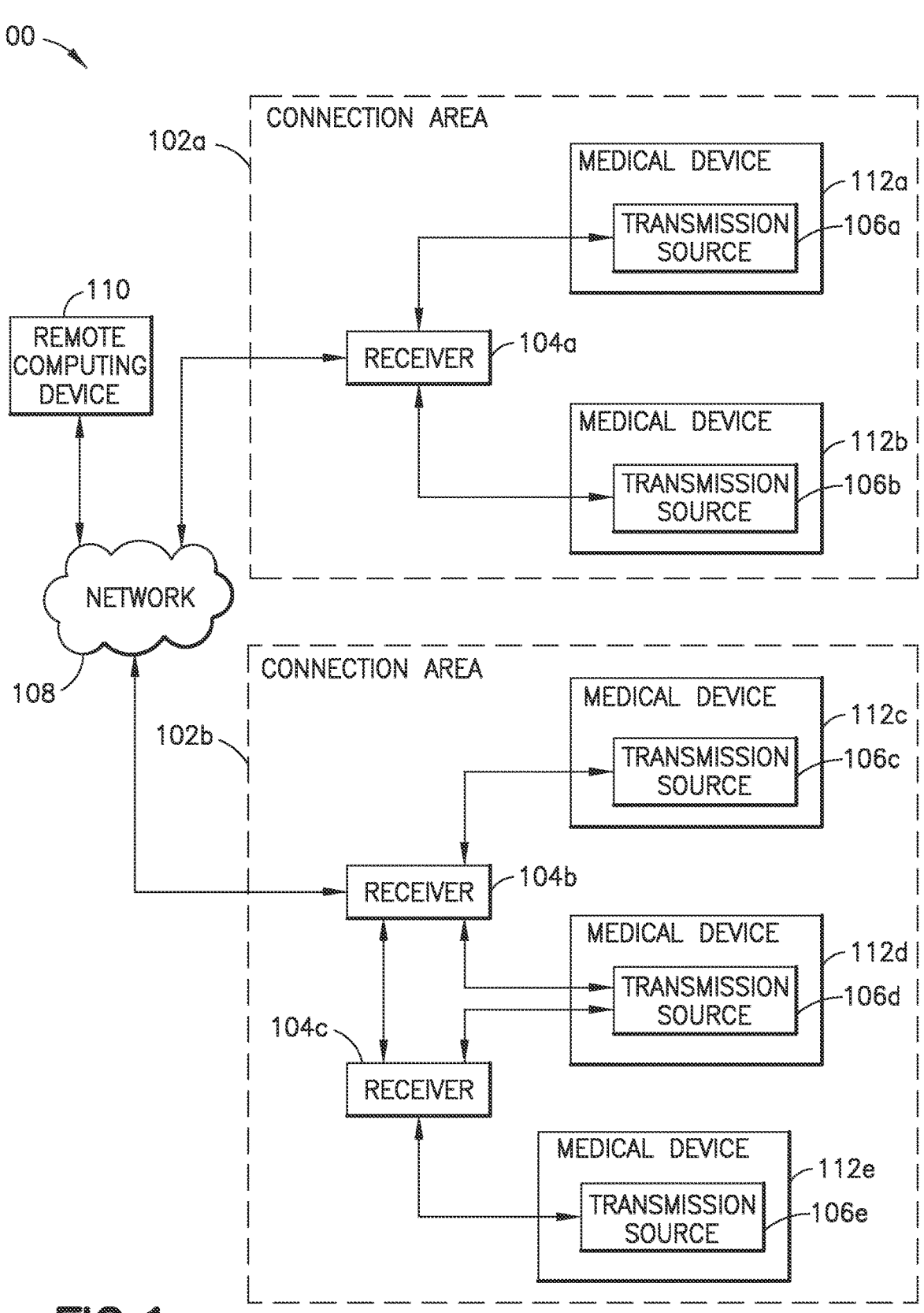
FIG. 1 is a diagram of a non-limiting embodiment or aspect of an environment in which systems, devices, products, apparatus, and/or methods, described herein, may be implemented according to embodiments or aspects of the present disclosure.

For purposes of the description hereinafter, the terms "end," "upper," "lower," "right," "left," "vertical," "horizontal," "top," "bottom," "lateral," "longitudinal," and derivatives thereof shall relate to the present disclosure as it is oriented in the drawing figures. However, it is to be understood that the present disclosure may assume various alternative variations and step sequences, except where expressly specified to the contrary. It is also to be understood that the specific devices and processes illustrated in the attached drawings, and described in the following specification, are simply exemplary embodiments or aspects of the present disclosure. Hence, specific dimensions and other physical characteristics related to the embodiments or aspects of the embodiments disclosed herein are not to be considered as limiting unless otherwise indicated.

No aspect, component, element, structure, act, step, function, instruction, and/or the like used herein should be construed as critical or essential unless explicitly described as such. Also, as used herein, the articles "a" and "an" are intended to include one or more items, and may be used interchangeably with "one or more" and "at least one." Furthermore, as used herein, the term "set" is intended to include one or more items (e.g., related items, unrelated items, a combination of related and unrelated items, etc.) and may be used interchangeably with "one or more" or "at least one." Where only one item is intended, the term "one" or similar language is used. Also, as used herein, the terms "has," "have," "having," or the like are intended to be open-ended terms. Further, the phrase "based on" is intended to mean "based at least in partially on" unless explicitly stated otherwise.

As used herein, the terms "communication" and "communicate" may refer to the reception, receipt, transmission, transfer, provision, and/or the like, of information (e.g., data, signals, messages, instructions, commands, and/or the like). For one unit (e.g., a device, a system, a component of a device or system, combinations thereof, and/or the like) to be in communication with another unit means that the one unit is able to directly or indirectly receive information from and/or transmit information to the other unit. This may refer to a direct or indirect connection (e.g., a direct communication connection, an indirect communication connection, and/or the like) that is wired and/or wireless in nature. Additionally, two units may be in communication with each other even though the information transmitted may be modified, processed, relayed, and/or routed between the first and second unit. For example, a first unit may be in communication with a second unit even though the first unit passively receives information and does not actively transmit information to the second unit. As another example, a first unit may be in communication with a second unit if at least one intermediary unit (e.g., a third unit located between the first unit and the second unit) processes information received from the first unit and communicates the processed information to the second unit. In some non-limiting embodiments, a message may refer to a network packet (e.g., a data packet, and/or the like) that includes data. It will be appreciated that numerous other arrangements are possible.

As used herein, the term "computing device" may refer to one or more electronic devices that are configured to directly or indirectly communicate with or over one or more networks. The computing device may be a mobile device. As used herein, the term "mobile device" may refer to one or more portable electronic devices configured to communicate with one or more networks. As an example, a mobile device may include a cellular phone (e.g., a smartphone or standard cellular phone), a portable computer (e.g., a tablet computer, a laptop computer, etc.), a wearable device (e.g., a watch, pair of glasses, lens, clothing, and/or the like), a personal digital assistant (PDA), and/or other like devices. The computing device may not be a mobile device, such as a desktop computer. Furthermore, the term "computer" may refer to any computing device that includes the necessary components to receive, process, and output data, and normally includes a display, a processor, a memory, an input device, and a network interface.

As used herein, a "data transmission apparatus" or a "transmission source" may refer to one or more devices, which may be used to transmit data or signals to a receiver in a connection area. For example, a data transmission apparatus or a transmission source may include one or more computers, peripheral devices, near-field communication (NFC) transmission sources, radio frequency identification (RFID) transmission sources, and/or other contactless transmission sources or transceivers, contact-based transmission sources, computers, servers, output devices, and/or the like.

As used herein, the term "receiver" may refer to one or more electronic devices or systems (e.g., located in a connection area and separate, remote from, and/or spaced apart from a data transmission apparatus or transmission source) used to receive data or signals from a data transmission apparatus or transmission source and configured to communicate with one or more networks. For example, a receiver may include one or more computers, portable computers, tablet computers, cellular phones, wearable devices (e.g., watches, glasses, lenses, clothing, and/or the like), PDAs, and/or the like. In some non-limiting embodiments or aspects, a receiver may include one or more computers, peripheral devices, near-field communication (NFC) reception sources, radio frequency identification (RFID) reception sources, and/or other contactless reception sources or transceivers, contact-based reception sources, computers, servers, input devices, and/or the like.

As used herein, the term "connection area" may refer to an area or location in which one or more receivers associated with that area or location are configured to receive data transmissions or signal transmissions from one or more data transmission apparatuses or transmission sources that are located within the connection area, have entered the connection, and/or are entering the connection area. For example, a connection area may be defined by a range of a wireless communication network between one or more receivers and one or more data transmission apparatuses or transmission sources.

As used herein, the term "server" may refer to one or more computing devices (e.g., processors, storage devices, similar computer components, and/or the like) that communicate with receivers, data transmission apparatuses or transmission sources, and/or other computing devices over a network (e.g., a public network, the Internet, a private network, and/or the like) and, in some examples, facilitate communication among other servers and/or receivers. It will be appreciated that various other arrangements are possible. As used herein, the term "system" may refer to one or more computing devices or combinations of computing devices (e.g., processors, servers, client devices, software applications, components of such, and/or the like). Reference to "a device," "a server," "a processor," and/or the like, as used herein, may refer to a previously-recited device, server, or processor that is recited as performing a previous step or function, a different server or processor, and/or a combination of servers and/or processors. For example, as used in the specification and the claims, a first server or a first processor that is recited as performing a first step or a first function may refer to the same or different server or the same or different processor recited as performing a second step or a second function.

As used herein, the term "application" or "application program interface" (API) refers to computer code, a set of rules, or other data sorted on a computer-readable medium that may be executed by a processor to facilitate interaction between software components, such as a client-side front-end and/or server-side back-end for receiving data from the client. An "interface" refers to a generated display, such as one or more graphical user interfaces (GUIs) with which a user may interact, either directly or indirectly (e.g., through a keyboard, mouse, etc.).

Non-limiting embodiments or aspects of the present disclosure are directed to systems, methods, and computer program products for identifying device connections in a connection area. Non-limiting embodiments or aspects of the present disclosure allow for identification of devices that are currently being or have previously been connected in an environment where there are multiple devices that can be simultaneously interconnected, without connecting devices directly communicating or interacting with each other. For example, non-limiting embodiments or aspects of the present disclosure provide a remote computing device and/or receiver that receives a plurality of physical parameters of a plurality of devices from a plurality of transmission sources in a connection area, and determines a physical connection state(s) between the plurality of devices based on the plurality of physical parameters of the plurality of devices. These features enable use of independent connection sensors that are sealed from the environment, creating a simplified workflow for caregivers, reducing a need and possibility for workarounds, eliminating RFID scanners as vectors of infection, providing increased detail regarding route of administration, monitoring of all points of entry that can result in fluid being delivered to a patient, and/or achieving higher reliability and specificity of radio detection. For example, these features enable determining which devices are interconnected without relying on physical connector type or restrictions on connections based on connector type or shape and/or without relying on electrical communication or interaction between connection sensors. These features further enable determining which devices are interconnected when multiple sets of connections may already be established.

Referring to FIG. 1, a non-limiting embodiment or aspect of an environment 100 in which systems, devices, products, apparatus, and/or methods, as described herein, may be implemented is shown. As shown in FIG. 1, environment 100 may include one or more connection areas 102, one or more receivers 104, a plurality of transmission sources 106, network 108, one or more remote computing devices 110, and/or a plurality of devices 112. For example, environment 100 as shown in FIG. 1 includes connection area 102a including receiver 104a and transmission sources 106a and 106b, and connection area 102b including receiver 104b, receiver 104c, and transmission sources 106c, 106d, and 106e. Transmission sources 106a through 106e may be respectively connected to or integrated with medical devices 112a through 112e. The number and arrangement of components shown in FIG. 1 are provided as an example. In some non-limiting embodiments or aspects, environment 100 may include additional components, fewer components, different components, or differently arranged components than those shown in FIG. 1. Additionally, or alternatively, a set of components (e.g., one or more components) may perform one or more functions described as being performed by another set of components of environment 100.

Figure 13:
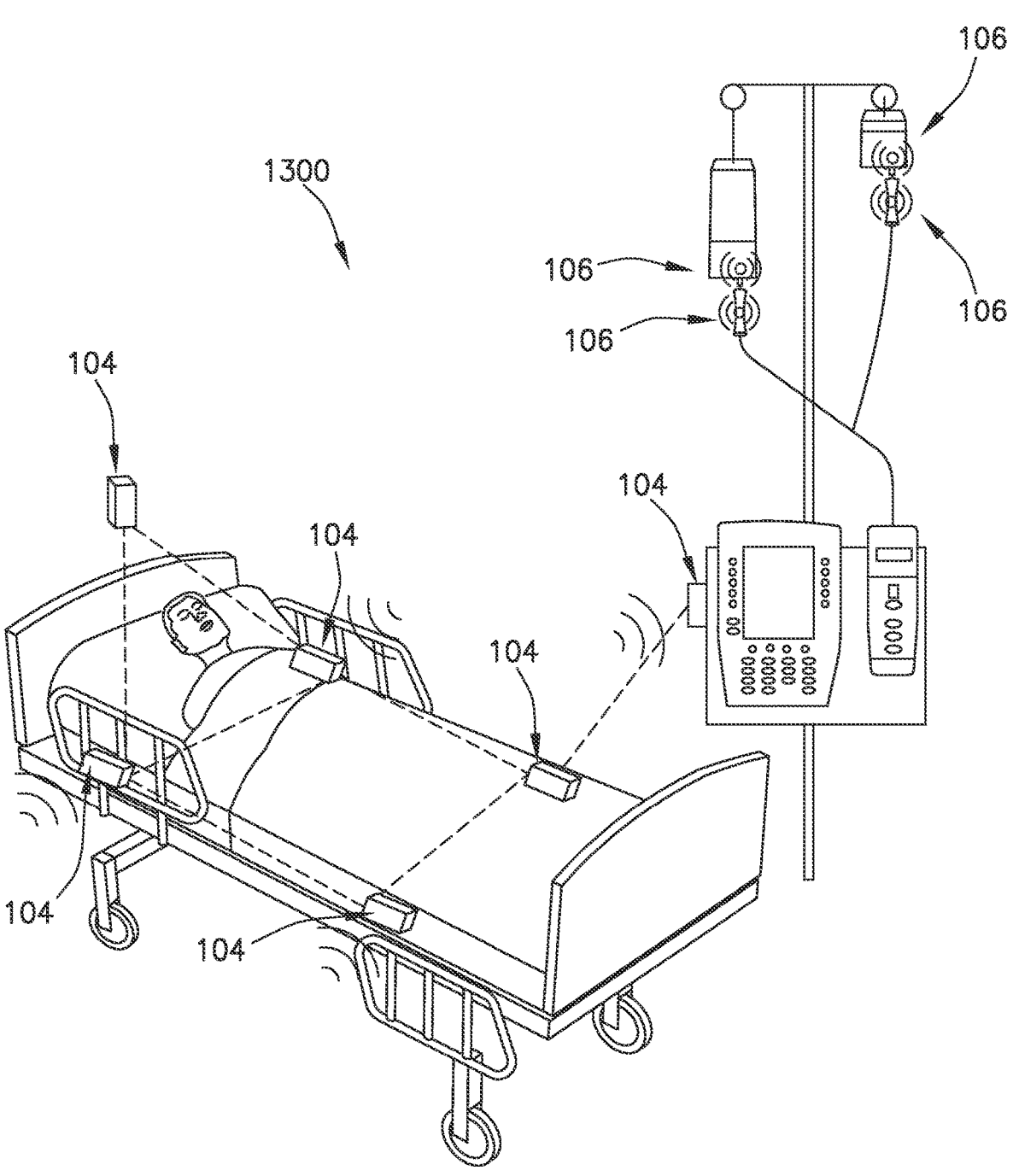
FIG. 13 is a diagram of an implementation of a non-limiting embodiment or aspect of the environment shown in FIG. 1.

In some non-limiting embodiments or aspects, a connection area 102 includes an area or location in which one or more receivers 104 are located and/or configured to communicate with transmission sources 106 via one or more wired and/or wireless networks. As an example, connection area 102a includes receiver 104a, and connection area 102b includes receivers 104b and 104c spaced apart from one another in the connection area. In some non-limiting embodiments or aspects, a connection area 102 includes an area or location defined or covered by a range of one or more short range wireless communication connections (e.g., an NFC communication connection, a Radio-frequency identification (RFID) communication connection, a Bluetooth® communication connection, and/or the like) via which one or more receivers 104 are capable of receiving information from transmission sources 106. For example, as shown in FIG. 13, multiple permanent and/or semi-permanent receivers 104 can be spaced apart from one another around a patient area, for example, connected to or integrated with objects such as a patient bed and an IV pump, to define a connection area 102 covering and/or surrounding the patient area, which can improve reliability and specificity of radio detection of transmission sources 106 within the patient area. Dotted lines between receivers 104 in FIG. 13 represent example communication connections between receivers 104.

In some non-limiting embodiments or aspects, a receiver 104 includes one or more devices capable of receiving information, data, and/or signals from and/or transmitting information, data, and/or signals to other receivers 104, transmission sources 106, and/or remote computing device 110 via one or more wired and/or wireless networks. As an example, a receiver 104 includes one or more computing devices, servers, desktop computers, mobile devices, chip readers, contactless transceivers, contactless receivers, NFC receivers, RFID receivers, contact based receivers, and/or the like. In some non-limiting embodiments or aspects, a mobile device includes one or more portable electronic devices configured to communicate with one or more other electronic devices via a network (e.g., network 108). For example, a mobile device can include a cellular phone (e.g., a smartphone or standard cellular phone), a portable computer (e.g., a tablet computer, a laptop computer, etc.), a wearable device (e.g., a watch, pair of glasses, augmented or virtual reality display, heads up display, clothing, and/or the like), a personal digital assistant (PDA), and/or other like devices. In some non-limiting embodiments or aspects, a receiver 104 includes one or more devices capable of receiving information from transmission sources 106 via a short range wireless communication connection (e.g., a communication connection that uses NFC protocol, a communication connection that uses Radio-frequency identification (RFID), a communication connection that uses a Bluetooth® wireless technology standard, and/or the like).

In some non-limiting embodiments or aspects, a receiver 104 is configured as a bedside unit that is capable of being located in a vicinity of a patient. For example, the bedside unit can be connected to a wall of a room of the patient, an IV pole, and/or a carrier held in place by a bed of the patient (e.g., between mattresses) near a side of the patient or the bed.

The bedside device can display warnings, as in the illustrations below, which can also have audible warnings. The bedside unit can also contain necessary networking interfaces and the RFID reader.

In some non-limiting embodiments or aspects, a transmission source 106 includes one or more devices capable of transmitting information, data, and/or signals to receivers 104 via one or more wired and/or wireless networks. For example, as shown in FIG. 1, transmission sources 106a and 106b communicate with receiver 104a, transmission sources 106c and 106d communicate with receiver 104b, and transmission sources 106d and 106e communicate with receiver 104c. As an example, a transmission source 106 includes one or more computing devices, chips, contactless transmitters, contactless transceivers, NFC transmitters, RFID transmitters, contact based transmitters, and/or the like. In some non-limiting embodiments or aspects, a transmission source 106 can include one or more devices capable of transmitting information to receivers 104 via a short range wireless communication connection (e.g., a communication connection that uses NFC protocol, a communication connection that uses Radio-frequency identification (RFID), a communication connection that uses a Bluetooth® wireless technology standard, and/or the like). In some non-limiting embodiments or aspects, transmission sources 106 may not be configured to communicate with one another. For example, transmission sources 106 may be configured to communicate only with receivers 104.

In some non-limiting embodiments or aspects, remote computing device 110 may include one or more devices capable of receiving information, data and/or signals from and/or transmitting information, data, and/or signals to one or more receivers 104, transmission sources 106, and/or other remote computing devices 110 via one or more wired and/or wireless networks. For example, remote computing device 110 may include a computing device, a server, a group of servers, a mobile device, a group of mobile devices and/or the like. In some non-limiting embodiments or aspects, remote computing device 110 includes one or more receivers 104. For example, remote computing device 110 includes a receiver 104 that enables remote computing device 110 to receive information directly from and/or communicate information directly to transmission sources 106 via a short range wireless communication connection (e.g., a communication connection that uses NFC protocol, a communication connection that uses Radio-frequency identification (RFID), a communication connection that uses a Bluetooth® wireless technology standard, and/or the like). In some non-limiting embodiments or aspects, remote computing device 110 may be separate from receivers 104 and/or remote from a connection area(s) 102.

In some non-limiting embodiments or aspects, remote computing device 110 is configured to receive information, data, and/or signals from and/or transmit information, data, and/or signals to receivers 104 in a plurality of different connection areas 102. For example, as shown in FIG. 1, receiver 104*a* may communicate with transmission sources 106*a* and 106*b* in connection area 102*a* via a short range wireless communication connection, and communicate with remote computing device 110 via network 108. Receivers 104*b* and 104*c* may communicate with each other in a connection area 102*b*. Receiver 104*b* may communicate with transmission sources 106*c* and 106*d*, and receiver 104*c* may communicate with transmission source 106*e*, which may be outside a connection range of receiver 104*b*, but still within connection area 102*b* due to being within a connection range of receiver 104*c*. Receiver 104*c* may communicate information and/or data received from transmission source 106*e* to receiver 104*b* for forwarding to remote computing device 110, or communicate the information and/or data directly to remote computing device 110 via network 108. Receivers 104 in a same connection area 102 may be associated with that connection area at remote computing device 110 and communicate with one another via network 108 or via one or more direct communication connections within that connection area 102, such as the short range communication connections as defined herein.

In some non-limiting embodiments or aspects, remote computing device 110 is configured to receive manually input information and/or data. As an example, if longer-term connections (e.g., if there are more than a single pair of devices) are out of sync, remote computing device 110 may receive a manual data entry that updates connections of devices. For example, manual data entry can occur if new IVs are started away from a bedside unit including receiver

104, e.g., outside a connection area 102. Remote computing system provides a user interface that enables a caregiver to manually update connections of devices if connections cannot be automatically determined. As an example, remote computing device 110 comprises buttons with a graphical user interface. One button is configured to control the remote computer 110 to cycle through connected devices, with the display graphically and/or alphanumerically indicating types of devices (or drug, ID number, etc.). Another button is configured to select a displayed device in the graphical user interface, via which a user can input device pairs into the remote computer 110.

In some non-limiting embodiments or aspects, network 108 includes one or more wired and/or wireless networks. For example, network 108 may include a cellular network (e.g., a long-term evolution (LTE) network, a third generation (3G) network, a fourth generation (4G) network, a code division multiple access (CDMA) network, etc.), a public land mobile network (PLMN), a local area network (LAN), a wide area network (WAN), a metropolitan area network (MAN), a telephone network (e.g., the public switched telephone network (PSTN)), a private network (e.g., a private network associated with a transaction service provider), an ad hoc network, an intranet, the Internet, a fiber optic-based network, a cloud computing network, and/or the like, and/or a combination of these or other types of networks.

Figures 2, 3:
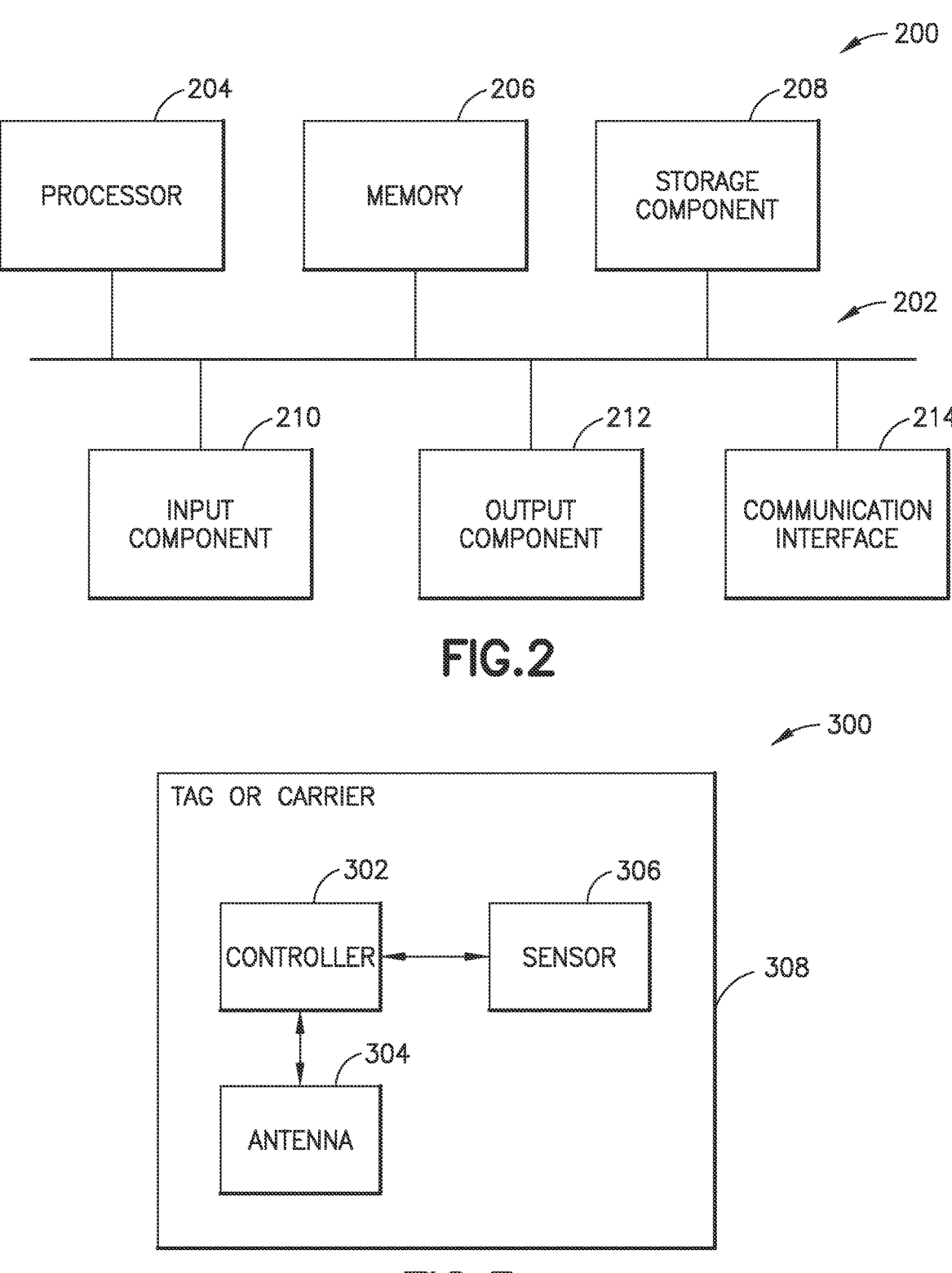
FIG. 2 is a diagram of a non-limiting embodiment or aspect of components of one or more devices of FIG. 1.
FIG. 3 is a diagram of a non-limiting embodiment or aspect of components of one or more devices of FIG. 1.

Referring now to FIG. 2, FIG. 2 is a diagram of example components of a device 200. Device 200 may correspond to receiver 104, transmission source 106, and/or remote computing device 110. In some non-limiting embodiments or aspects, receiver 104, transmission source 106, and/or remote computing device 110 may include at least one device 200 and/or at least one component of device 200. As shown in FIG. 2, device 200 may include bus 202, processor 204, memory 206, storage component 208, input component 210, output component 212, and/or communication interface 214.

Bus 202 may include a component that permits communication among the components of device 200. In some non-limiting embodiments or aspects, processor 204 may be implemented in hardware, firmware, or a combination of hardware and software. For example, processor 204 may include a processor (e.g., a central processing unit (CPU), a graphics processing unit (GPU), an accelerated processing unit (APU), etc.), a microprocessor, a digital signal processor (DSP), and/or any processing component (e.g., a field-programmable gate array (FPGA), an application-specific integrated circuit (ASIC), etc.), and/or the like, which can be programmed to perform a function. Memory 206 may include a random-access memory (RAM), a read only memory (ROM), and/or another type of dynamic or static storage device (e.g., a flash memory, a magnetic memory, an optical memory, etc.) that stores information and/or instructions for use by processor 204.

Storage component 208 may store information and/or software related to the operation and use of device 200. For example, storage component 208 may include a hard disk (e.g., a magnetic disk, an optical disk, a magneto-optic disk, a solid state disk, etc.), a compact disc (CD), a digital versatile disc (DVD), a floppy disk, a cartridge, a magnetic tape, and/or another type of computer-readable medium, along with a corresponding drive.

Input component 210 may include a component that permits device 200 to receive information, such as via user input (e.g., a touch screen display, a keyboard, a keypad, a mouse, a button, a switch, a microphone, etc.). Additionally, or alternatively, input component 210 may include a sensor for sensing information (e.g., a global positioning system (GPS) component, an accelerometer, a gyroscope, an actuator, etc.). Output component 212 may include a component that provides output information from device 200 (e.g., a display, a speaker, one or more light-emitting diodes (LEDs), etc.).

Communication interface 214 may include a transceiver-like component (e.g., a transceiver, a separate receiver and transmission source, etc.) that enables device 200 to communicate with other devices, such as via a wired connection, a wireless connection, or a combination of wired and wireless connections. Communication interface 214 may permit device 200 to receive information from another device and/or provide information to another device. For example, communication interface 214 may include an Ethernet interface, an optical interface, a coaxial interface, an infrared interface, a radio frequency (RF) interface, a universal serial bus (USB) interface, a Wi-Fi interface, a cellular network interface, and/or the like.

Device 200 may perform one or more processes described herein. Device 200 may perform these processes based on processor 204 executing software instructions stored by a computer-readable medium, such as memory 206 and/or storage component 208. A computer-readable medium (e.g., a non-transitory computer-readable medium) is defined herein as a non-transitory memory device. A memory device includes memory space located inside of a single physical storage device or memory space spread across multiple physical storage devices.

Software instructions may be read into memory 206 and/or storage component 208 from another computer-readable medium or from another device via communication interface 214. When executed, software instructions stored in memory 206 and/or storage component 208 may cause processor 204 to perform one or more processes described herein. Additionally, or alternatively, hardwired circuitry may be used in place of or in combination with software instructions to perform one or more processes described herein. Thus, embodiments or aspects described herein are not limited to any specific combination of hardware circuitry and software.

The number and arrangement of components shown in FIG. 2 are provided as an example. In some non-limiting embodiments or aspects, device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

Referring now to FIG. 3, FIG. 3 is a diagram of example components of a tracking device 300. Tracking device 300 may be implemented as a transmission source 106 and/or a transmission source 106 may be included as part of tracking device 300. For example, tracking device 300 comprises controller 302, e.g., an RFID chip, antenna 304, e.g., an RFID antenna, and/or sensor 306, which can be attached to or integrated with a tag or carrier 308 configured to carry or hold the components of the tracking device 300. Device 300 may be connected to and/or integrated with another device, such as a medical device 112. For example, tracking device 300 may be connected to and/or integrated with at least one of the following: a syringe, an IV spike, an IV access site, an IV bag, an IV set, a catheter, a medical device connector, or any combination thereof. In some non-limiting embodiments or aspects, tracking device 300 is located within a fluid flow path formed by one or more medical devices.

In some non-limiting embodiments or aspects, tracking device 300 receives power via a wirelessly transmitted power source, such as via an RF transmission from a receiver 104. In some non-limiting embodiments or aspects, tracking device 300 includes an integrated power source, such as a battery.

In some non-limiting embodiments or aspects, sensor 306 is configured to sense an electrical, optical, and/or physical state or characteristic. As an example, sensor 306 is configured to sense electrically, optically, and/or physically at least one physical parameter of a medical device 112 with which tracking device 300 is connected and/or integrated. In some non-limiting embodiments or aspects, sensor 306 comprises a pressure sensor. For example, sensor 306 is configured to sense a pressure applied to a connection of a medical device 112 when the medical device 112 is connected to another medical device 112. In some non-limiting embodiments or aspects, sensor 306 is integrated with and/or included as part of controller 302.

In some non-limiting embodiments or aspects, tracking device 300 and/or sensor 306 are located or positioned at or near a fluid entry point or a fluid exit point of a medical device 112. As an example, tracking device 300 and/or sensor 306 are connected to and/or integrated with a connector of a medical device 112 configured to connect to another connector of another medical device such that when the connector of the medical device is connected to or disconnected from the another connector of the another medical device, the another connector of the another medical device activates or actuates sensor 306, e.g., by applying or removing a pressure on a pressure and/or increasing or decreasing a transmissivity of a light path to an optical sensor.

In some non-limiting embodiments or aspects, controller 302 is configured to control antenna 304 to transmit information, data, and/or signals. As an example, controller 302 is configured to transmit information based on the at least one physical parameter sensed by the sensor 302. Controller 302 may include a storage component storing an identifier that identifies a type of medical device and/or uniquely identifies a medical device with which tracking device 300 is connected and/or integrated, and/or other information and/or data related to the medical device and/or a procedure for which the medical device is intended to be used. For example, controller 302 transmits the identifier and/or other information and/or data with the information and/or data including the sensed at least one physical parameter.

In some non-limiting embodiments, controller 302 is configured to control antenna 304 to transmit information including the sensed at least one physical parameter in response to at least one of the following: entering a connection area, (e.g., in response to receiving a polling signal from a receiver 104), receiving a polling signal from a receiver 104 while within a connection area, actuation of sensor 306, determining a change in a physical parameter sensed by sensor 306, or any combination thereof. In some non-limiting embodiments or aspects, after an initial transmission in response to polling by a receiver 104 upon entering a connection area, controller 302 is configured to control antenna 304 to transmit information including the sensed at least one physical parameter only in response to actuation of sensor 306 and/or a change in a physical parameter sensed by sensor 306. In some non-limiting embodiments or aspects, controller 302 is configured to control antenna 304 to transmit information including the sensed at least one physical parameter continuously while
tracking device 300 is within a connection area 102 or at
periodic intervals while tracking device 300 is within a
connection area 102.

In some non-limiting embodiments or aspects, controller
302, antenna 304, and/or sensor 306 are sealed from the
environment and/or self-contained. For example, controller
302, antenna 304, and sensor 306 are sealed within and/or
integrally formed within tag or carrier 308. In some non-
limiting embodiments or aspects, controller 302, antenna
304, sensor 306, and/or tag or carrier 308 are sealed within
and/or integrally formed within another device. For
example, tracking device 300 is sealed within and/or inte-
grally formed with a medical device.

The number and arrangement of components shown in
FIG. 3 are provided as an example. In some non-limiting
embodiments or aspects, tracking device 300 may include
additional components, fewer components, different com-
ponents, or differently arranged components than those
shown in FIG. 3. Additionally, or alternatively, a set of
components (e.g., one or more components) of tracking
device 300 may perform one or more functions described as
being performed by another set of components of device
300.

Figure 4:
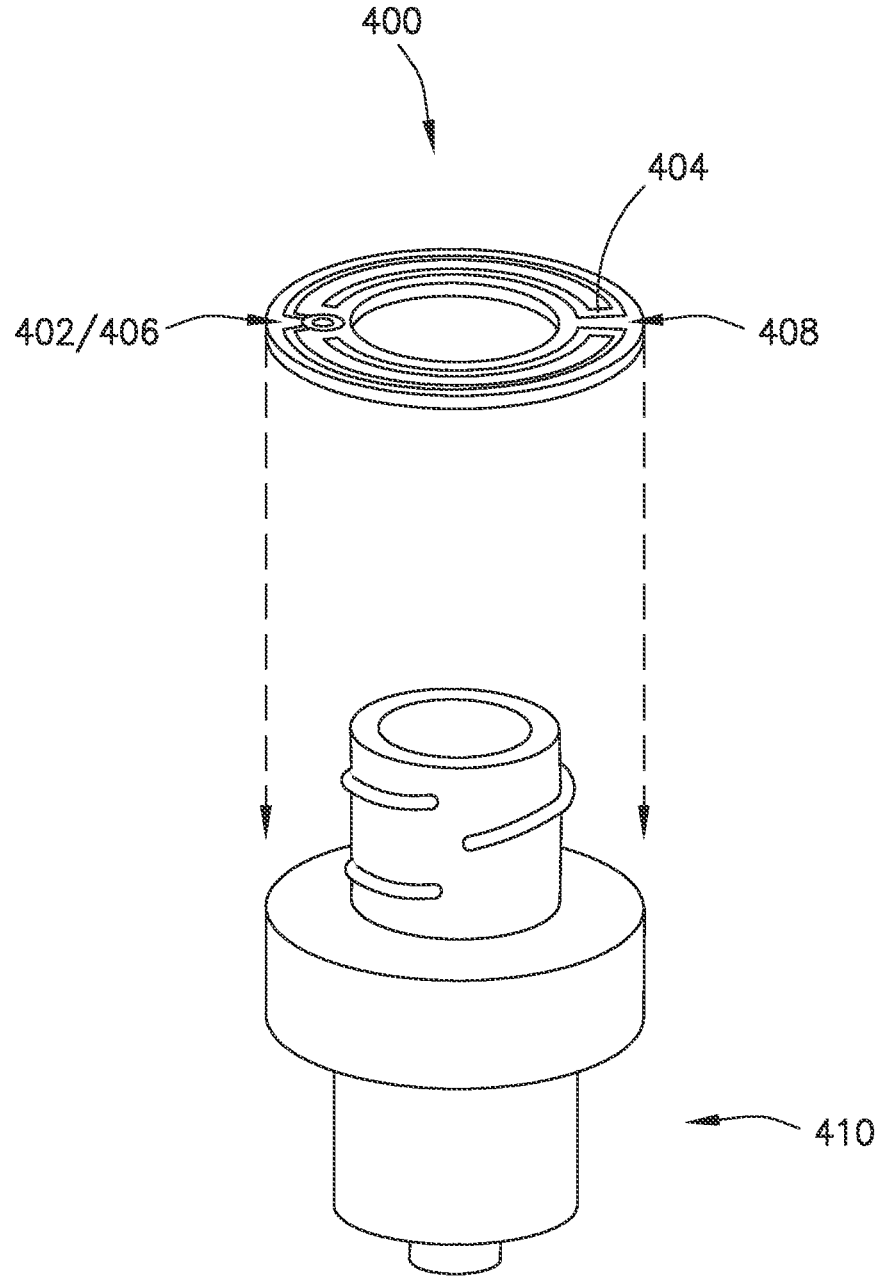
FIG. 4 is a perspective view of an implementation of a non-limiting embodiment or aspect of components of one or more devices of FIG. 3.

FIG. 4 is a perspective view of a non-limiting embodi-
ment or aspect of an implementation 400 relating to tracking
device 300 shown in FIG. 3. As shown in FIG. 4, tracking
device 400 may include controller 402, antenna 404, and
sensor 406 provided on tag or carrier 408. In some non-
limiting embodiments or aspects, controller 402 may be the
same as or similar to controller 302 as described herein,
antenna 404 may the same as or similar to antenna 304 as
described herein, sensor 406 may be the same as or similar
to sensor 306 described herein, and tag or carrier 408 may
be the same as or similar to tag or carrier 308 described
herein.

In some non-limiting embodiments or aspects, tracking
device 400 is configured to be connected or adhered to a
medical device, such as a medical connector 410 as shown
in FIG. 4. For example, tag or carrier 408 of tracking device
400 can comprise an adhesive and/or mechanical connector,
such as a push-fit connection, a snap-fit connection, and the
like, configured to connect tracking device 400 to medical
connector 410.

In some non-limiting embodiments or aspects, medical
connector 410 forms or is configured to form at least a
portion of a fluid flow path, and tracking device 400 is
attached to medical connector 410 at a fluid outlet or a fluid
inlet of medical connector 410. In some non-limiting
embodiments or aspects, antenna 404 may be located adja-
cent to other components on the tag or carrier 408, such as
controller 402 and sensor 406, to simplify manufacturing
and assembly. However, other geometries and adhesive
technologies may be used. For example, as shown in FIG. 4,
tag or carrier 408 including antenna 404 may comprise a ring
shape configured to be applied over a base of medical
connector 410, which can enable use of a larger antenna
without significantly increasing a size of tracking device
400. Sensor 406 may comprise a layer in the ring-shaped tag
or carrier 408, for example, a layer on top of a layer
comprising antenna 402. In some non-limiting embodiments
or aspects, tracking device 400 can be implemented as an
RFID chip including an RFID antenna and a pressure sensor.

Figure 5:
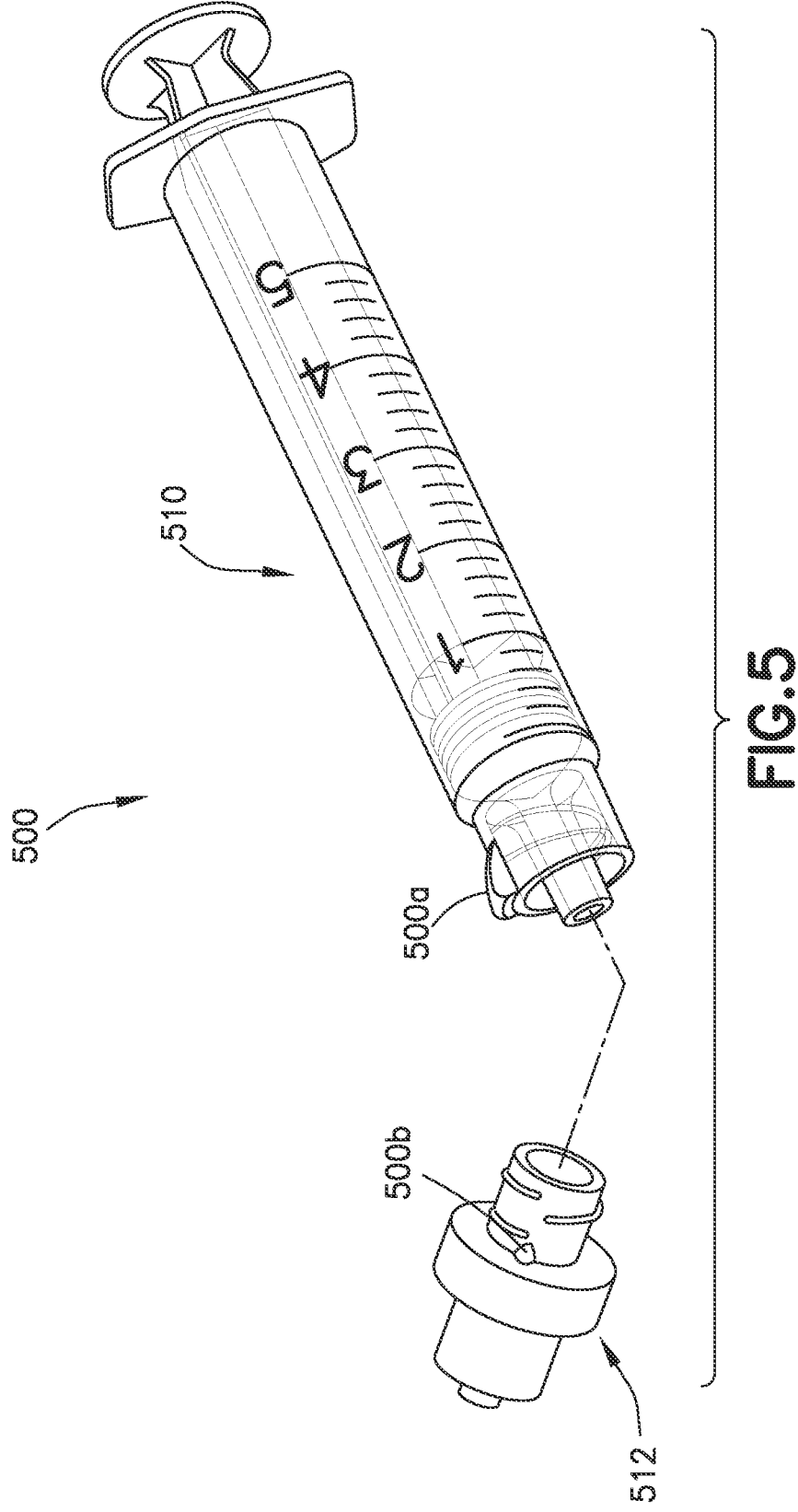
FIG. 5 is a perspective view of an implementation of a non-limiting embodiment or aspect of components of one or more devices of FIG. 3.

FIG. 5 is a perspective view of a non-limiting embodi-
ment or aspect of an implementation 500 relating to tracking
device 300 shown in FIG. 3. In some non-limiting embodi-
ments or aspects, tracking device 500 may be the same as or similar to tracking device 300 as described herein. In some
non-limiting embodiments or aspects, tracking device 500 is
sealed within and/or integrally formed within another
device. For example, as shown in FIG. 5, first tracking
device 500a is sealed within syringe 510 and second track-
ing device 500b is sealed within Luer connector 512.

FIGS. 6A-6E are perspective views of non-limiting
embodiments or aspects of an implementation 600 relating
to tracking device 300 shown in FIG. 3. As shown in FIGS.
6A-6E, tracking device 600 may include controller 602,
antenna 604, and sensor 606 provided on tag or carrier 608.
In some non-limiting embodiments or aspects, controller
602 may be the same as or similar to controller 302 as
described herein, antenna 604 may the same as or similar to
antenna 304 as described herein, sensor 606 may be the
same as or similar to sensor 306 described herein, and tag or
carrier 608 may be the same as or similar to tag or carrier
308 described herein.

Figures 6A, 6B:
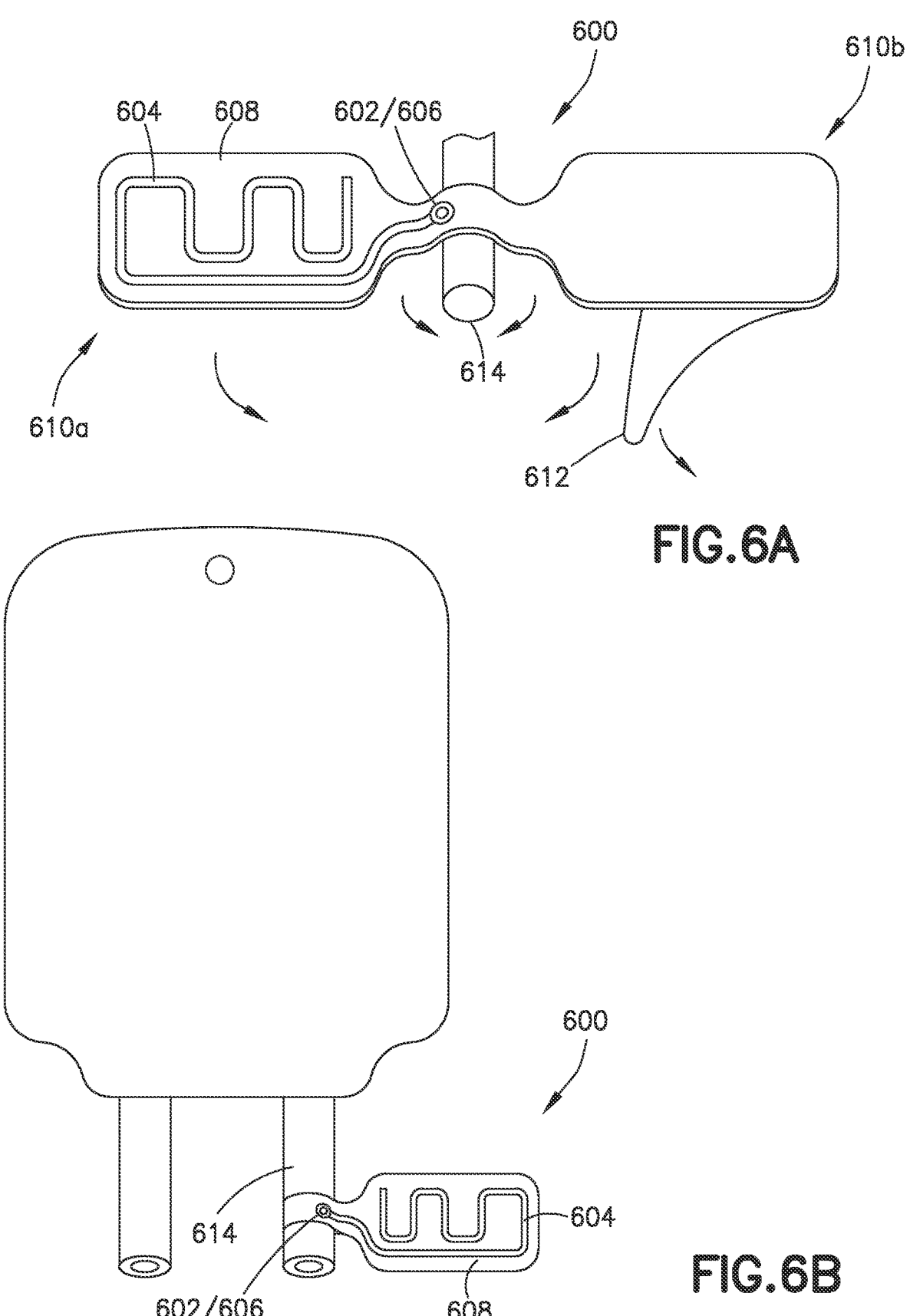
FIG. 6A is a perspective view of an implementation of a non-limiting embodiment or aspect of components of one or more devices of FIG. 3.
FIG. 6B is a perspective view of an implementation of a non-limiting embodiment or aspect of components of one or more devices of FIG. 3.
Figure 6C:
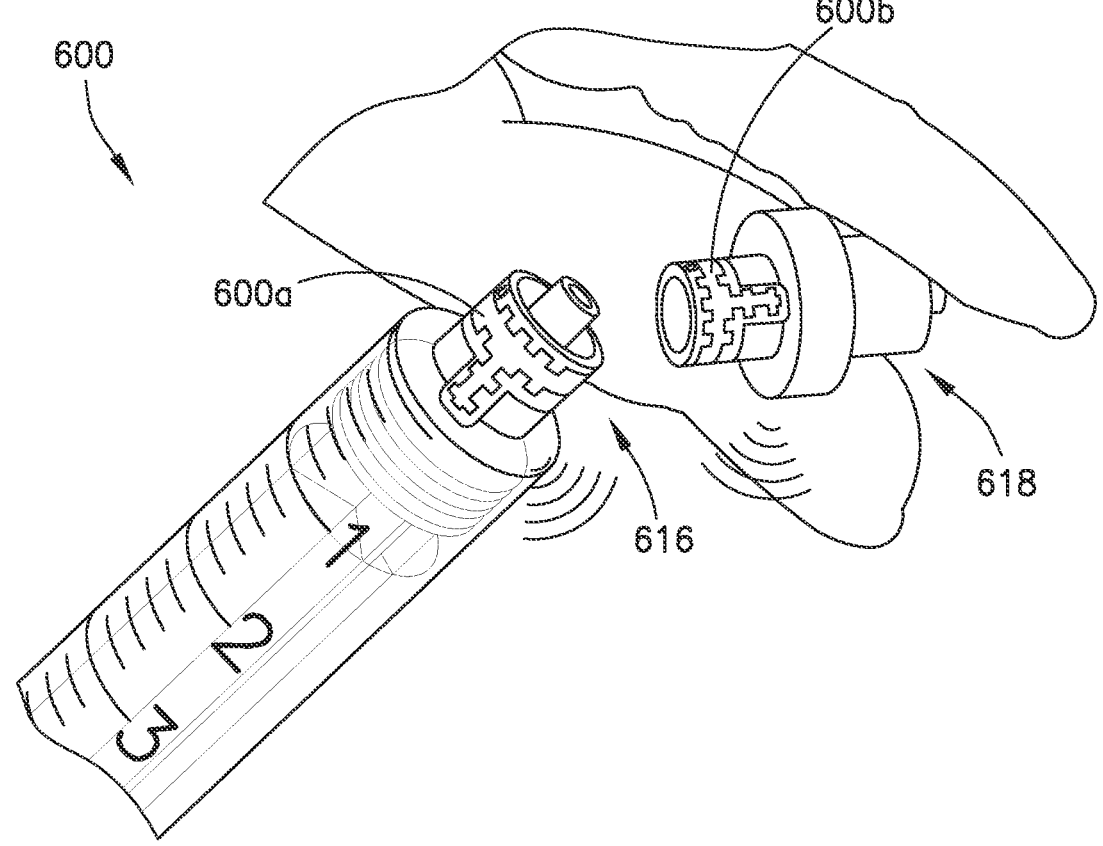
FIG. 6C is a perspective view of an implementation of a non-limiting embodiment or aspect of components of one or more devices of FIG. 3.
Figure 6D:
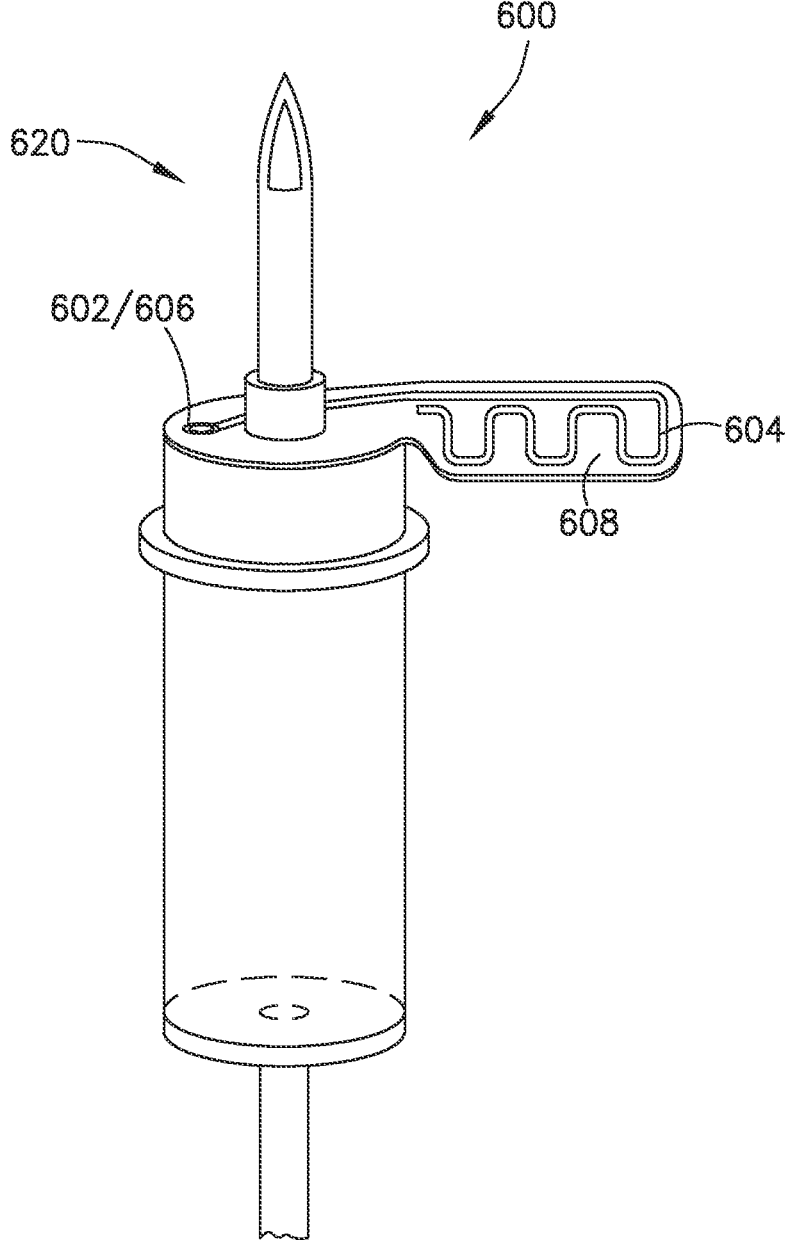
FIG. 6D is a perspective view of an implementation of a non-limiting embodiment or aspect of components of one or more devices of FIG. 3.
Figure 6E:
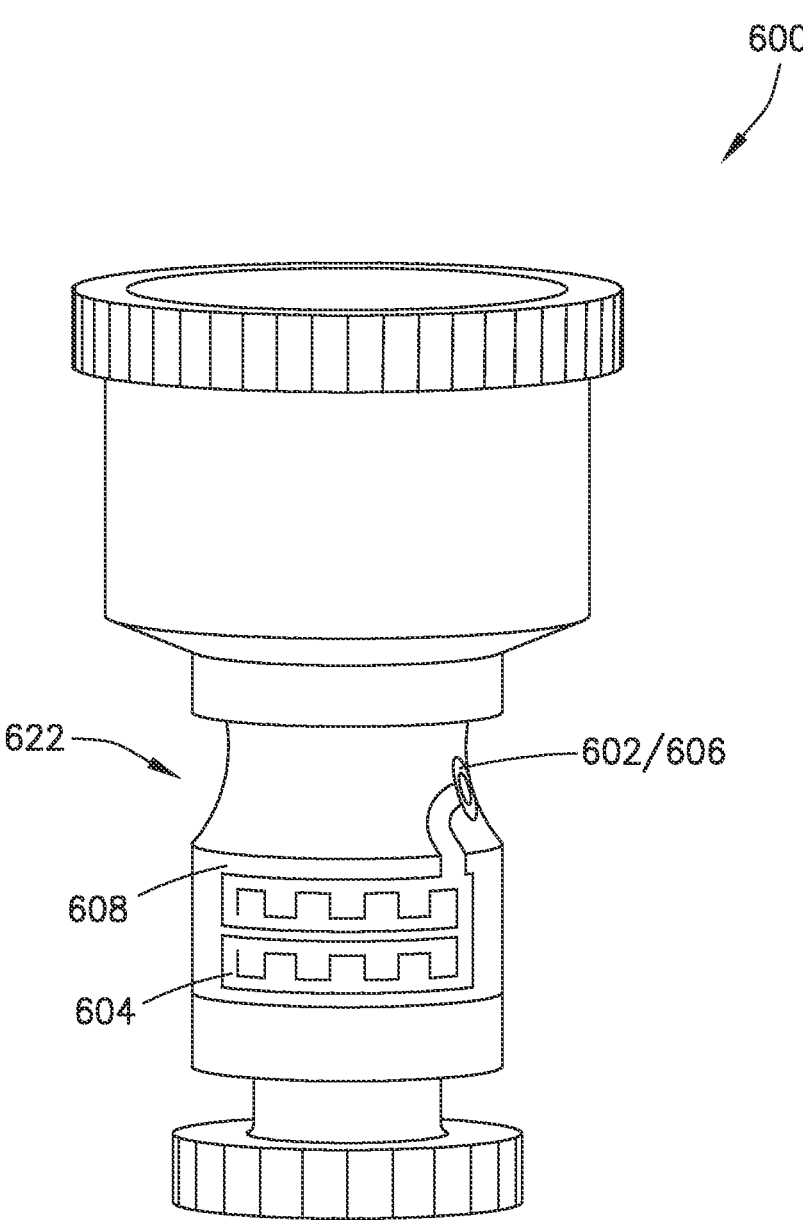
FIG. 6E is a perspective view of an implementation of a non-limiting embodiment or aspect of components of one or more devices of FIG. 3.

In some non-limiting embodiments or aspects, as shown
in FIG. 6A, tracking device 600 comprises tag or carrier 608
including wings 610a and 610b. As an example, tag or
carrier 608 is flexible so that tag or carrier 608 can be
wrapped or bent around a medical device, such as IV bag
connector 614, syringe 616, Luer connection of IV set 618,
IV bag access spike 620, closed system transfer device 622,
and the like. For example, wings 610a and 610b comprise
removable adhesive backing 612 such that when adhesive
backing 612 is removed and wings 610a and 610b are
connected to one another with tag or carrier 608 wrapped
around a medical device, such as around IV bag connector
614 as shown in FIG. 6A, tracking device 600 is secured to
the medical device. FIG. 6B shows tracking device 600
attached to IV bag connector 614. FIG. 6C shows first
tracking device 600a attached to a Luer connection of
syringe 616 and second tracking device 600b attached to a
Luer connection of IV set 618 to be connected to the Luer
connection of syringe 616. As an example, Luer connection
of syringe 616 activates or actuates a sensor of tracking
device 600b when connected to or disconnected from Luer
connection of IV set 618, and Luer connection of IV set 618
activates or actuates a sensor of tracking device 600a when
connected to or disconnected from Luer connection of
syringe 616. For example, tracking devices 600a and 600b
are positioned or located proximate openings or ends of the
Luer connectors such that a pressure on or an amount of light
received by sensors of the tracking devices 600a or 600b
changes with IV set 618 and syringe 616 are connected and
disconnected from one another. FIG. 6D shows tracking
device 600 attached to IV bag access spike 620. FIG. 6E
shows tracking device 600 wrapped around a closed system
transfer device connector 622.

Figure 7:
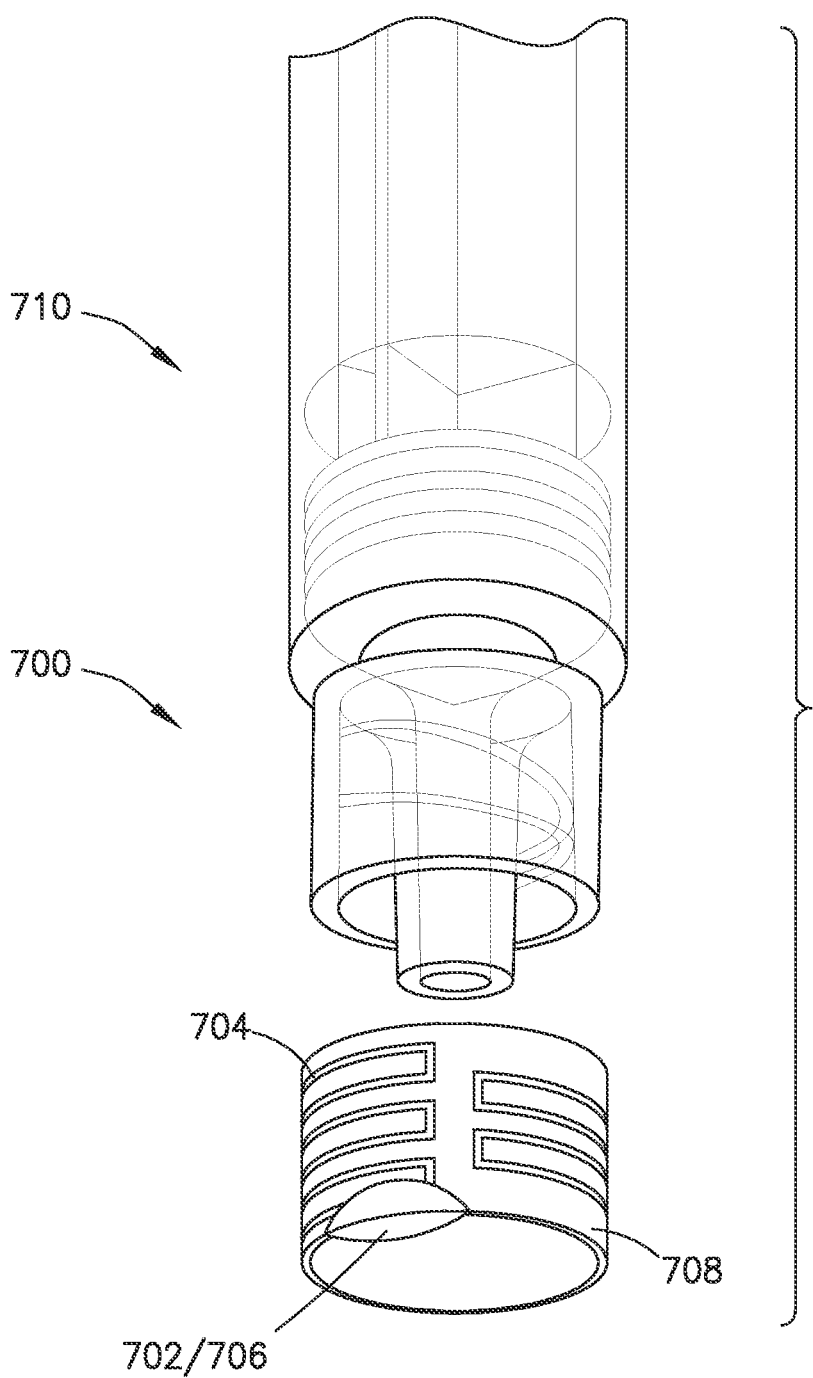
FIG. 7 is a perspective view of an implementation of a non-limiting embodiment or aspect of components of one or more devices of FIG. 3.

FIG. 7 is a perspective view of a non-limiting embodi-
ment or aspect of an implementation 700 relating to tracking
device 300 shown in FIG. 3. As shown in FIG. 7, tracking
device 700 may include controller 702, antenna 704, and
sensor 706 provided on tag or carrier 708. In some non-
limiting embodiments or aspects, controller 702 may be the
same as or similar to controller 302 as described herein,
antenna 704 may the same as or similar to antenna 304 as
described herein, sensor 706 may be the same as or similar
to sensor 306 described herein, and tag or carrier 708 may
be the same as or similar to tag or carrier 308 described
herein.

In some non-limiting embodiments or aspects, as shown
in FIG. 7, tracking device 700 comprises a sleeve having a
cylindrical shape. For example, as shown in FIG. 7, tag or
carrier 708 is configured to be applied around syringe 710 and/or around a Luer connector of syringe 710. Sensor 706 may be located at a distal end of the cylindrically shaped sleeve such that sensor 706 is located proximate a distal end of the Luer connector of syringe 410 when tracking device 700 is connected to the syringe 710 so that sensor 706 is configured to be physically actuated in response to connection of the Luer connector of syringe 710 to another medical device.

Referring now to FIG. 8, a process 800 is shown for identifying device connections in a connection area. In some non-limiting embodiments or aspects, one or more of the steps of process 800 may be performed (e.g., completely, partially, etc.) by one or more receivers 104. In some non-limiting embodiments or aspects, one or more of the steps of process 800 may be performed (e.g., completely, partially, etc.) by another system, another device, another group of systems, or another group of devices, separate from or including one or more receivers 104, such as remote computing device 110 and/or transmission sources 106. In some non-limiting embodiments or aspects, one or more of the steps of process 800 may be performed (e.g., completely, partially, etc.) by receiver 104, which may be a computing device, such as a tablet computer, that executes cloud-based software that provides a user interface and delivers cloud-based APIs to the receiver 104.

As shown in FIG. 8, process 800 includes a step 802 of receiving, with at least one processor, a plurality of physical parameters of a plurality of devices from a plurality of transmission sources in a connection area, wherein the plurality of physical parameters indicates physical states of the plurality of devices. At a step 804, at least one processor determines at least one physical connection state between the plurality of devices based on the plurality of physical parameters of the plurality of devices. At a step 806, at least one processor monitors and/or controls the plurality of devices based on the at least one physical connection state between the plurality of devices.

In some non-limiting embodiments or aspects, a physical parameter of a device may change according to a physical state of the device. As described herein, a device may comprise a medical device, such as one or more of the following: a syringe, an IV spike, an IV access site, an IV bag, an IV set, a catheter, a medical device connector, or any combination thereof. In some non-limiting embodiments or aspects, a physical parameter can indicate a finite set of states of a physical state of a device. For example, a physical parameter may indicate a connected state or a disconnected state of a device, such as a catheter connected or disconnected state with a patient and/or an IV set, a syringe connected or disconnected state with an IV set, and the like. In some non-limiting embodiments or aspects, a physical parameter can indicate a magnitude of change in a physical state of a device. For example, a physical parameter may indicate a level or a strength of a connection of a device, for example, from a fully disconnected level to a fully connected level. A level of a connection that is less than a fully connected level may indicate an incorrect or improper connection of a device to another device. For example, a pressure sensor may sense a pressure at a Luer connection of a syringe as a physical parameter, and a sensed pressure less than a threshold pressure may indicate that the syringe is not fully connected or is improperly connected to another device, such as an IV set.

In some non-limiting embodiments or aspects, the plurality of physical parameters is associated with a plurality of event times, wherein the plurality of event times indicates times of changes in the physical states of the plurality of devices. As an example, at least one first event time may be associated with at least one first device physical parameter, (e.g., activation of a first device and/or a sensor associated with the first device), and at least one second event time may be associated with at least one second device physical parameter, (e.g., activation of a second device and/or a sensor associated with the first device). For example, a transmission source 106 automatically updates and/or transmits a physical parameter in response to a change in the physical parameter, for example, in response to activation of a device 112 and/or a sensor 306 of a tracking device 300 associated with a device 112, and/or transmits an updated physical parameter in response to polling from a receiver 104. In some non-limiting embodiments, a transmission sources 106 transmits an event time associated with the updated physical parameter. In some non-limiting embodiments, a receiver 104 determines an event associated with the updated physical parameter based on a time at which a signal including the updated physical parameter is received.

In some non-limiting embodiments or aspects, the plurality of physical parameters indicate a plurality of different physical states of the plurality of devices. For example, a first physical parameter may indicate an optically sensed physical state of a device, such as a covered Luer connection of a syringe, and a second physical parameter may indicate a physically sensed physical state of a device, such as a pressure on a Luer connection of a syringe. In some non-limiting embodiments or aspects, a physical parameter may include information that indicates at least one predetermined connection state between two or more connectors of a plurality of connectors of at least one device.

For example, a physical parameter may indicate a valve open state or a valve closed state of a valve between connection ports of an IV set. In some non-limiting embodiment or aspects, a physical parameter may be associated with a device identifier that uniquely identifies a device, a connector of a device, a type of device, or any combination thereof. For example, a device identifier may uniquely identify one or more of the following: a type of IV set, the IV set from all other IV sets of that type, individual connectors or connections of the IV set, or any combination thereof. As an example, if it is not physically possible to form a connection, but it is determined that a connection has been made based on the physical parameters and/or event times, device identifiers can be used to further characterize the connection. For example, by comparing device identifiers associated with devices determined as connected, it can be determined that a detection or system error condition has occurred, devices are being misused, and/or simultaneous connections are being made between two or more pairs of devices and correct pairings can be determined.

In some non-limiting embodiments or aspects, at least one physical parameter of the plurality of physical parameters includes a plurality of connection parameters that indicates physical states of a plurality of connectors of at least one device of the plurality of devices. For example, at least one device of the plurality of devices may comprise a plurality of connectors configured to be physically connected to at least one of the following: a patient, the at least one second device, at least one third device, one or more connectors of the at least one second device, one or more connectors of the at least one third device, or any combination thereof, and the at least one physical parameter physical parameter may include a plurality of connection parameters that indicates physical states of the plurality of connectors of the at least one device. For example, an IV set may include a first connector at a first end of a flow path and a second connector at a second end of the flow path, wherein a physical state of the first connector is indicated by a first physical parameter sensed by a first sensor and a physical state of the second connector is indicated by a second physical parameter sensed by a second sensor.

Referring now to FIG. 9, a process 900 is shown for identifying device connections in a connection area. In some non-limiting embodiments or aspects, one or more of the steps of process 900 may be performed (e.g., completely, partially, etc.) by one or more transmission sources 106 and/or tracking devices 300. In some non-limiting embodiments or aspects, one or more of the steps of process 900 may be performed (e.g., completely, partially, etc.) by another system, another device, another group of systems, or another group of devices, separate from or including one or more transmission sources 106 and/or tracking devices 300, such as remote computing device 110 and/or one or more receivers 104.

As shown in FIG. 9, process 900 includes a step 902 of sensing, with a plurality of sensors on the plurality of devices, the physical states of the plurality of devices to determine the plurality of physical parameters. For example, at least one first sensor on at least one first device may sense at least one physical state of the at least one first device to determine at least one first physical parameter of the at least one first device, and at least one second sensor on at least one second device may sense at least one physical state of the at least one second device to determine at least one second physical parameter of the at least one second device. In a step 904, a plurality of transmission sources on the plurality of devices transmit the plurality of physical parameters. For example, at least one first transmission source on the at least one first device may transmit the at least one first physical parameter of the at least one first device, and at least one second transmission source on the at least one second device may transmit the at least one second physical parameter of the at least one second device.

In some non-limiting embodiments or aspects, a transmission source 106 transmits physical parameters in response to entering a connection area, in response to receiving a polling signal, and/or in response to a change in a physical state of a device associated with the transmission source 106. As an example, the at least one first transmission source may transmit the at least one first physical parameter in response entering the connection area, and the at least one second transmission source may transmit the at least one second physical parameter in response to entering the connection area. As an example, an RFID transmission source may automatically transmit a physical parameter upon entering a connection area, e.g., in response to being polled by an RFID reader. The RFID transmission source may continuously transmit the physical parameter while in the connection area, transmit the physical parameter at periodic intervals while in the connection area, and/or transmit the physical parameter only in response to actuation of a sensor of the RFID transmission source after an initial transmission in response to polling by an RFID reader upon entering in the connection area. In some non-limiting embodiments or aspects, the at least one first transmission source may transmit the at least one first physical parameter in response to the at least one first sensor sensing a change in the at least one physical state of the at least one first device, and the at least one second transmission source may transmit the at least one second physical parameter in response to the at least one second sensor sensing a change in the at least one physical state of the at least second first device. For example, a transmission source 106 transmits a physical parameter in response to a sensor 306 of a tracking device 300 that implements the transmission source 106 sensing a change in a physical state of a device associated with the transmission source 106.

Referring now to FIG. 10, a process 1000 is shown for identifying device connections in a connection area. In some non-limiting embodiments or aspects, one or more of the steps of process 1000 may be performed (e.g., completely, partially, etc.) by one or more receivers 104. In some non-limiting embodiments or aspects, one or more of the steps of process 1000 may be performed (e.g., completely, partially, etc.) by another system, another device, another group of systems, or another group of devices, separate from or including one or more receivers 104, such as remote computing device 110 and/or transmission sources 106. In some non-limiting embodiments or aspects, one or more of the steps of process 1000 may be performed (e.g., completely, partially, etc.) by a receiver 104, which may be a computing device, such as a tablet computer, that executes cloud-based software that provides a user interface and delivers cloud-based APIs to the receiver 104.

As shown in FIG. 10, process 1000 includes a step of 1002 of determining, with at least one processor, a device event associated with a connection area. At a step 1004, at least one processor determines an effect of the device event. At a step 1006, at least one processor updates a device register based on the determined effect of the device event.

In some non-limiting embodiments or aspects, a device register includes a list of devices, also referred to herein as nodes, in a connection area. Devices in the list are identified by device identifiers, and device identifiers are stored in association with physical parameters associated with the devices, event times associated with the physical parameters, and/or indications of connections and/or disconnections between devices. The information in a device register can be used to build or generate a computer-based logical branch structure of physical devices in a connection area. As an example, a logical branch structure maps to a physical branch structure in the connection area and includes nodes corresponding to points of entry into the physical device structure. For example, a logical branch structure of a physical branch structure for a physical IV branch structure including a fluid flow path includes nodes at points of entry to the fluid flow path, e.g., at fluid inputs and fluid outputs. A logical branch structure may include predetermined device associations or connections, e.g., between nodes/ends of a catheter, and/or detected device associations or connections, e.g., between a syringe and a node/end of the catheter connected in the connection area.

In some non-limiting embodiments or aspects, step 1002 includes receiving a device identifier and/or at least one physical parameter associated with at least one device of the plurality of devices. For example, a receiver 104 determines a device event in response to receiving a signal including the at least one physical parameter and the device identifier associated with the at least one device. Step 1004 may include determining that the at least one device of the plurality of devices is within the connection area. As an example, a receiver 104 compares the device identifier of the device with a current device register including a list of devices in the connection area to determine if the device associated with the device identifier is already registered or is a new device that has entered the connection area. Step 1006 may include updating the device register including the list of devices in the connection area with the device identifier in association with the at least one physical parameter of the at least one device and/or reporting the updated device register to at least one remote computing system. A device identifier can be stored in the device register in association with any other information or data associated with the at least one device and/or received in a signal associated with the device identifier, e.g., information or data received from or associated with a transmission source, a connection area, a patient identifier of a patient, a medication identifier of a medication, or any combination thereof.

In some non-limiting embodiments or aspects, step 1002 includes polling the connection area and determining responses to the polling. As an example, a receiver 104 polls a connection area 102 and determines a device event in response the polling. For example, a receiver receives responses from transmission sources 106 associated with devices currently in the connection area, but the receiver 104 does not receive responses from transmission sources 106 outside the connection area during the polling. Step 1004 may include determining based on the responses to the polling an updated list of devices currently in the connection area. For example, if the at least one device is listed in the device register, but does not respond to the polling within a predetermined polling time period, a receiver 104 determines that the at least one device is no longer in the connection area. Step 1006 may include updating the device register to remove the device identifier of the at least one device from the device register, updating connections of any devices identified as connected to the at least one device in the device register as described herein in more detail below, and/or reporting the updated device register to at least one remote computing system.

In some non-limiting embodiments or aspects, step 1002 includes receiving the plurality of physical parameters in association with a plurality of event times (e.g., a time stamp associated with a change in a physical parameter sensed by a corresponding sensor and/or a time stamp associated with transmission of a physical parameter by a corresponding transmission source) and/or associating the plurality of physical parameters with event times as the plurality of physical parameters are received (e.g., a time stamp associated with a reception of a physical parameter by a receiver). As an example, the plurality of physical parameters is associated with a plurality of event times, and the plurality of event times indicates times of changes in the physical states of the plurality of devices. For example, a tracking device 300 as described herein and connected to a syringe activates when the syringe is connected to an IV connector (e.g., a female Luer), which causes the syringe tracking device 300 to transmit a signal to a receiver 104. Similarly, a tracking device 300 as described herein and connected to the IV connector activates when the IV connector is connected to the syringe (e.g., a male Luer), which causes the IV connector tracking device 300 to transmit a signal to a receiver 104. A receiver 104 may determine a device event in response to receiving a signal including a physical parameter in association with an event time.

In some non-limiting embodiments, at step 1004, at least one physical connection state between the plurality of devices is determined based at least partially on the plurality of event times. As an example, at least one processor determines whether the plurality of event times are within a sliding time window. For example, when two or more device events happen within a predetermined time interval with compatible devices (e.g., compatibility as indicated by device identifiers), a connection of the two or more devices can be determined. A receiver 104 and/or remote computing device 110 can determine if the two or more events happen within a sliding time window. As an example, at least one first event time associated with the at least one first device physical parameter and at least one second event time associated with the at least one second device physical parameter are received, and the at least one connection state is determined based on the at least one first even time and the at least one second event time. For example, if the at least one first event time and the at least one second event time each occur within a predetermined time of each other, e.g., 2 seconds, the receiver 104 and/or remote computing device 110 determines that the two or more devices associated with the at least one first even time and the at least one second event time are associated with one another.

In some non-limiting embodiments or aspects, the at least one connection state between the plurality of devices is determined based at least partially on at least one predefined compatibility of the plurality of devices. As an example, when device identifiers for two or more devices are received within a sliding time window, a receiver 104 and/or remote computing device 110 determines based on the device identifiers whether the two or more devices are compatible with one another. For example, the receiver 104 and/or remote computing device 110 can consult a look-up of acceptable states and connections for devices associated with the device identifiers. If the two or more devices are determined to be incompatible, the receiver 104 and/or remote computing device 110 can issue an alert that the two or more devices, which are associated with one another, are being misused. If the two or more devices are determined to be compatible, the receiver 104 and/or remote computing device 110 can determine a connection between the two devices and update the device register to include an indication of the connection in association with the device identifiers of the devices, a time of the connection, and/or physical parameters of the devices.

In some non-limiting embodiments or aspects, the plurality of physical parameters include information or data indicating a connection state of the plurality of physical devices. For example, a physical parameter can indicate a connected state, a disconnected state, and/or a level of connection of a device and/or a node or connector of a device. If the physical parameters associated with the at least one first event time and the at least one second event time indicate connected states, a receiver 104 and/or remote computing device 110 determines that the devices are now connected and updates the device register. If the physical parameters associated with the at least one first event time and the at least one second event time indicate disconnected states, the receiver 104 and/or remote computing device 110 determines that the devices are now disconnected.

It is noted herein that in addition to the detection of various states of connection/disconnection, the system can also be utilized to monitor preparation and/or maintenance of the fluid path. For example, other events that can be captured include disinfection of a component of the system, capping/decapping of a component of the system, and monitoring placement of component into or out of the system (such as monitoring placement of a catheter securement device). It is also contemplated herein that the system can detect additional disinfection processes, such as the preparation of an IV site with an antimicrobial agent.

If the physical parameters associated with the at least one first event time and the at least one second event time indicate non-matching states (e.g., a disconnected state and a connected state) and/or a level of connection below a threshold connection level, the receiver 104 and/or remote computing device 110 determines an error condition and provides an alert based on the error condition. As an example, a receiver 104 and/or remote computing device 110 compares the device identifiers of the two or more devices having device events within the sliding time window to the device register to determine if the devices are currently associated or connected. If the devices are currently connected, the receiver 104 and/or remote computing device 110 determines that the devices are now disconnected based on the at least one first event time and the at least one second event time occurring within the predetermined time of each other. If the devices are not currently connected in the device register, the receiver 104 and/or remote computing device 110 determines that the devices are now associated and/or connected to one another. In some non-limiting embodiments or aspects, a receiver determines whether a disconnection of two or more devices is a permissible disconnection, (e.g., by consulting a look-up table of acceptable states and connections associated with the device identifiers). For example, if physical parameters for the two or more devices, which are stored as connected in the device register, are received that indicate different states, e.g., a connected state and a disconnected state, a receiver 14 determines an error condition and outputs an alert indicating that a detection or system error condition has occurred and/or that the two medical devices are being misused. Furthermore, the system can send data from other sensors that detect problems with a system component, such as a catheter, an IV set, and/or a patient. The system can provide healthcare workers with alerts for errors or other clinical issues, system analytics, and workflow based on data from the system.

In some non-limiting embodiments or aspects, a receiver 104 and/or remote computing device 110 associated with a connection area can filter or reject signals from transmission sources associated with devices of neighboring patients (e.g., devices in other connection areas). Due to complexities in RF signal propagation, device events that occur in other connection areas may sometimes be improperly detected. As an example, a receiver 104 and/or remote computing device 110 can compare a device identifier of a signal received from a transmission source to a device register for another connection area(s) to determine whether the transmission source and/or a medical device associated with the transmission source are registered in the other connection area and/or associated or connected to another device within the other connection area. If the device is already registered and/or connected in the other connection area, the receiver 104 and/or remote computing device 110 can reject registration of the device in the connection area associated with the receiver 104. In some non-limiting embodiments or aspects, a connection area is associated with a predefined list of acceptable devices, and the receiver 104 and/or remote computing device 110 compares the device identifier of a signal received from a transmission source to the list of acceptable devices to determine whether the transmission source and/or a medical device associated with the transmission source can be registered in that connection area and/or connected to another device within that connection area.

Referring again to FIG. 8, in some non-limiting embodiments or aspects, step 806 includes controlling a flow of a fluid in a fluid flow path including at least one device of the plurality of devices based at least partially on the at least one physical connection state between the plurality of devices. For example, by using a device register including physical structures of medical devices and connections between medical devices, including where transmission sources are located relative to the physical fluid flow path, a tree structure of the fluid flow path, (e.g., IV system) is established, e.g., a logical branch structure. A receiver 104 and/or remote computing device 110 monitor each point of entry to the fluid flow path that enables fluid to be delivered to the patient. For example, sensors at each point of entry, which may be sensors 306 of tracking devices 300 or separate sensors configured to communicate sensed data associated with the fluid flow path to the receiver 104 and/or remote computing device 110, and the receiver 104 and/or remote computing device 110 can issue an alert and/or control one or more devices in the fluid flow path to stop the fluid flow and/or adjust the fluid flow, e.g., using one or more electronically controlled valves, based on the sensed data, e.g., in response sensed data indicating that devices in the fluid flow path have been disconnected.

In some non-limiting embodiments or aspects, step 806 includes receiving a patient identifier associated with a patient, receiving a medication identifier of a medication to be delivered to the patient via the fluid flow path, associating the patient identifier and the medication identifier with the at least one device of the fluid flow path and controlling the flow of the fluid in the fluid flow path based at least partially on the patient identifier and the medication identifier. As an example, sensors at each point of entry to the fluid flow path, which may be sensors 306 of tracking devices 300 or separate sensors configured to communicate sensed data associated with the fluid flow path to the receiver 104 and/or remote computing device 110, are configured to determine at least one of the following: a connection state at a point of entry, a volume of fluid in the fluid flow path and/or at a point of entry, a type of fluid or medication in the fluid flow path and/or at the point of entry, a flow rate of fluid in the fluid flow path and/or at a point of entry, or any combination thereof. For example, a receiver 104 and/or remote computing device 110 compare medication, medication dosage, medication delivery route, and/or medication delivery time determined based on the sensed data to an approved patient, approved medication, approved medication dosage, approved medication delivery route, and/or approved medication delivery time associated with the patient identifier and/or the medication identifier to reduce medication administration errors. The receiver 104 and/or remote computing device 110 can issue an alert and/or control one or more devices in the flow path to stop fluid flow and/or adjust fluid flow based on the sensed data, the patient identifier, and/or the medication identifier. For example, if a medication sensed at a point of entry in the fluid flow path is determined to be an improper medication for the patient, an improper dosage for the patient and/or medication, an improper medication delivery route for the patient and/or medication (e.g., improper point of entry to the fluid flow path), and/or an improper medication delivery time for the patient and/or medication, the receiver 104 and/or remote computing device 110 can issue an alert and/or control one or more devices in the flow path to stop the fluid flow.

In some non-limiting embodiments or aspects, step 806 includes generating, with at least one processor, a digital representation of a fluid flow path including at least one device of the plurality of devices based at least partially on the at least one physical connection state between the plurality of devices; and monitoring, with at least one processor, a flow of a fluid in the fluid flow path based at least partially on the representation of the fluid flow path. As an example, the at least one processor can control an audio and/or visual output device to output an audible and/or visible indication in the connection area, wherein the audible and/or visible indication indicates a status of the fluid flow path. For example, the receiver 104 and/or remote computing device 110 can generate a logical IV branch structure that maps to a physical IV branch structure in the connection area and includes a unique node identifier for each medical device of the physical IV branch structure, each connector or entry/exit point to a fluid flow path formed by the medical devices, and/or each element of a medical device associated with an action that can affect the fluid flow path, (e.g., a valve in a medical device), in a connection area. The logical IV branch structure includes connections between nodes, which can be nodes connected in the connection area and/or predetermined node connections, such as nodes associated with a same medical device and/or nodes connected outside the connection area that enter the connection area already connection to one another. An example physical IV branch structure mapped to a logical IV branch structure is described in more detail herein below with respect to FIG. 12.

Figure 11A:
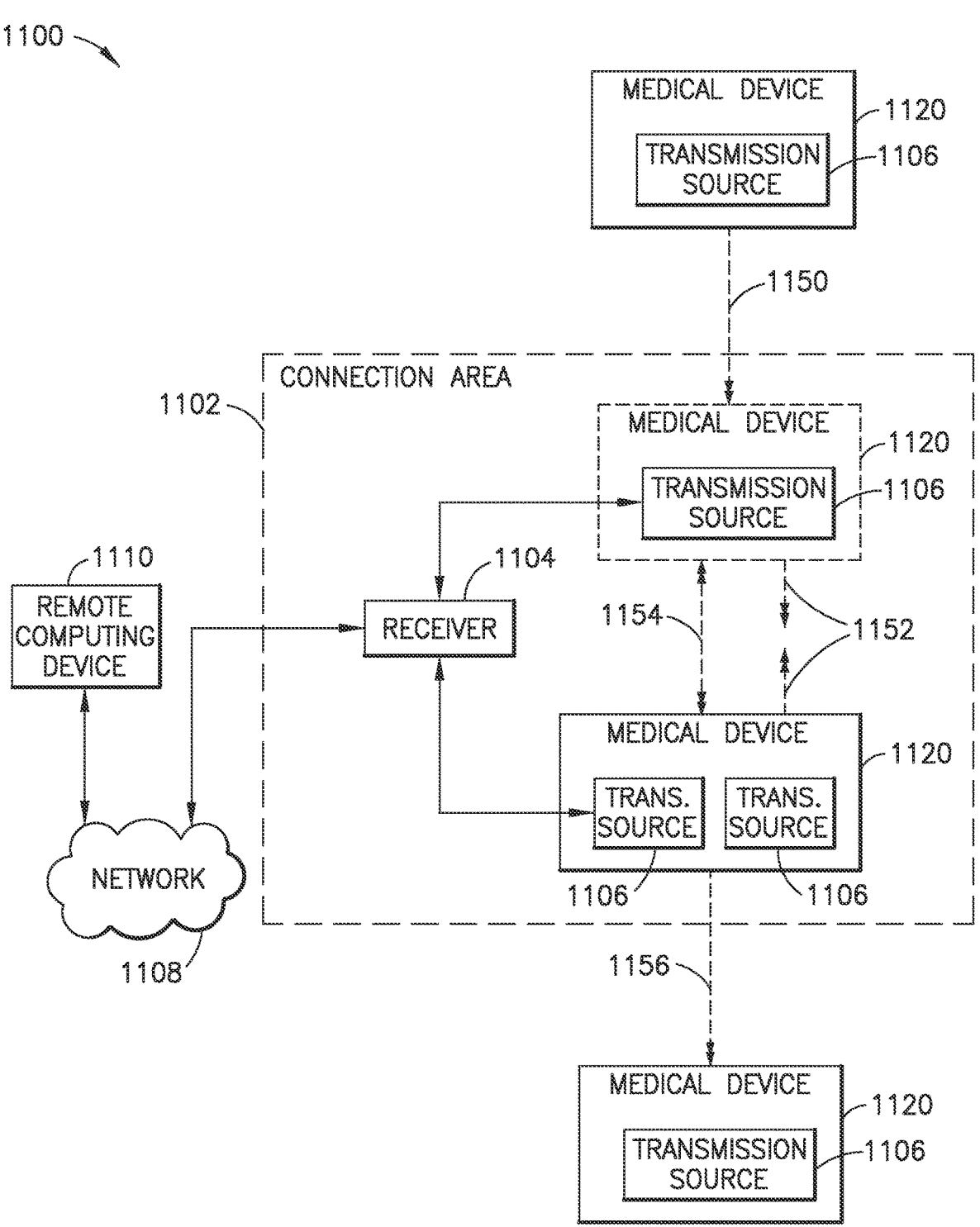
FIG. 11A is a diagram of an overview of an implementation of a non-limiting embodiment or aspect of processes shown in FIGS. 8-10.

FIG. 11A is a diagram of an overview of a non-limiting embodiment or aspect of an implementation 1100 relating to processes 800, 900, and 1000 shown in FIGS. 8-10. As shown in FIG. 11A, implementation 1100 may include connection area 1102, receiver 1104, transmission sources 1106 associated with medical devices 1120, network 1108, and/or remote computing device 1110. In some non-limiting embodiments or aspects, connection area 1102 may be the same as or similar to connection area 102 as described herein above, receiver 1104 may the same as or similar to receiver 104 as described herein above, transmission sources 1106 may be the same as or similar to transmission sources 106 and/or tracking devices 300 described herein above, network 1108 may be the same as or similar to network 108 as described herein above, and remote computing device 1110 may be the same as or similar to remote computing device 110 as described herein above.

It is noted that implementation 1100 is described primarily with respect to receiver 1104 performing one or more functions referenced by reference numbers in FIG. 11A; however, additionally, or alternatively, a remote system or server, such as remote computing device 1110, or one or more other receivers in communication with receiver 1104, such as a receiver configuration of implementation 1300 as shown in FIG. 13, or a cloud-based server of a cloud-based receiver in which receiver 1104 comprises a user device, such as a tablet computer, that communicates with the cloud-based server, may perform one or more functions referenced by the reference numbers in FIG. 11A.

Figure 11B:
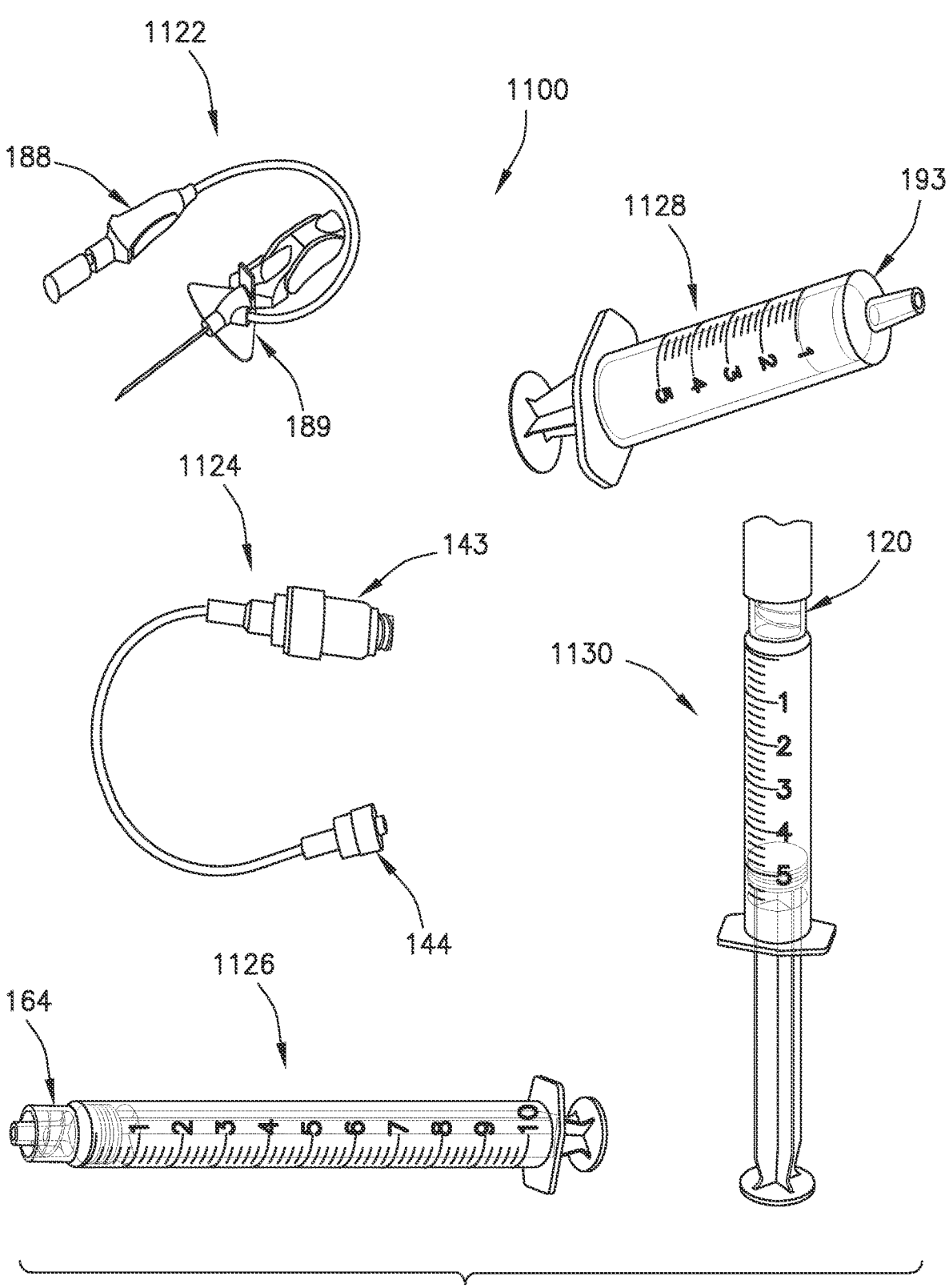
FIG. 11B is a diagram of example devices of an implementation of a non-limiting embodiment or aspect of processes shown in FIGS. 8-10.

FIG. 11B is a diagram of devices of implementation 1100. As shown in FIG. 11B, implementation 1100 includes medical devices 1120 comprising IV catheter 1122, IV set 1124, first drug syringe 1126, second drug syringe 1128, and flush syringe 1130. Each medical device 1120 has a transmission device 1106, e.g., a tracking device 300 as shown in FIG. 3, at each node where a fluid connection can be made, e.g., at each fluid inlet and each fluid outlet, and each tracking device or node is associated with a unique device or node identifier. The tracking devices at each node are referred to herein with the same numerical label as associated with the corresponding node identifiers of the tracking devices in FIG. 11B. For example, IV catheter 1122 comprises tracking devices associated with node identifiers 188 and 189, IV set 1124 comprises tracking devices associated with node identifiers 143 and 144, first drug syringe 1126 comprises a tracking device associated with node identifier 164, second drug syringe 1128 comprises a tracking device associated with node identifier 193, and flush syringe 1130 comprises a tracking device associated with node identifier 120. The tracking devices or nodes 188, 189, 143, 144, 164, 193, and 120 are located at fluid entry points and fluid exit points of the medical devices 1120.

FIG. 11C is a table of example data of implementation 1100. FIG. 11C shows an example device register database, which is populated as time progresses, with data received from and processed by receiver 1104 and/or remote computing device 1110 associated with connection area 1102. Time index, which can be any number of seconds per interval, is mapped to a time range on a real-time clock. Device Register is a listing of devices within connection area 1102 in association with the physical parameters of the devices. Coincidence Logic indicates when device nodes are associated with one another, (e.g., x+y indicates association of device nodes x and y, x−y indicates disassociation of device nodes x and y).

Referring now to FIGS. 11A-C, as shown by reference number 1150 in FIG. 11A, a medical device 1120 enters connection area 1102. For example, at time index 2035 in FIG. 11C, there are no medical devices in the connection area 1102, e.g., there are no medical devices 1120 listed in the device register. At time index 2036, catheter 1122 enters the connection area. Receiver 1104 receives a signal from the tracking devices associated with node identifiers 188 and 189, e.g., in response to polling from receiver 1104, including the node identifiers 188 and 189 and a physical parameter associated with each node identifier, and updates the device register with the node identifiers 188 and 189 in association with inactive states. For example, in implementation 1100 a physical parameter indicates that a node identifier associated with the physical parameter is in one of an active state, e.g., a data bit 1, and an inactive state, e.g., a data bit 0. Node identifiers 188 and 189 are associated with inactive state 0 by receiver 1104 in the device registered based on the received physical parameters.

At time index 2038, catheter 1122 is placed or deployed. For example, a cannula of catheter 1122 associated with node identifier 189 is inserted into a patient. A sensor of the tracking device associated with node identifier 189 is activated in response to deployment of the catheter, which causes the tracking device associated with node identifier 189 to transmit a signal including node identifier 189 associated with a physical parameter indicating an active state of the node 189. Receiver 1104 receives the signal, determines that no other node identifiers with active state physical parameters were received within a sliding time window, e.g., within 2 seconds of receipt of the signal associated with node identifier 189, determines that an active state physical parameter associated with node identifier 189 without node identifier 189 being associated with another node identifier is permissible for node identifier 189, (e.g., by consulting a look-up table of acceptable states and connections for node identifiers/devices), and updates the device register to include node identifier 189 associated with active state 1 and node identifier 188 associated with inactive state 0.

At time index 2040, IV set 1124 including tracking devices associated with node identifiers 143 and 144 enters the connection area 1102, and node identifiers 143 and 144 are added to the device register in associated with inactive state 0, for example, in a manner similar to that as described herein above with respect to reference number 1150.

As shown by reference number 1152 in FIG. 11A, a medical device 1120 is connected with another medical device 1120 in connection area 1102. For example, at time index 2041, IV set 1124 is connected to catheter 1122. For example, a connector of catheter 1122 associated with node identifier 188 is connected to a connector of IV set 1124 associated with node identifier 144. Sensors of the tracking devices associated with node identifiers 188 and 144 are activated in response to the connection, e.g., a pressure is applied to pressure sensors of the tracking devices by connectors of the connecting devices, which causes the tracking devices associated with node identifiers 188 and 144 to respectively transmit a signal including node identifier 188 associated with a physical parameter indicating an active state 1 of the node 188 and a signal including node identifier 144 associated with a physical parameter indicating an active state 1 of the node 144. Receiver 1104 receives the signals, determines that the signals were generated, transmitted and/or received within the sliding time window, e.g., within 2 seconds of each other, determines that a connection of node identifier 188 and 144 is a permissible connection, (e.g., by consulting a look-up table of acceptable states and connections for node identifiers/devices), and updates the device register to include node identifier 188 associated with active state 1 and node identifier 144 associated with active state 1, and to include an indication that node 188 and node 144 are connected to one another, e.g., coincidence logic 188+144.

At time index 2046, first drug syringe 1126 including a tracking device associated with node identifier 164 enters the connection area 1102, and node identifier 164 is added to the device register in association with inactive state 0, for example, in a manner similar to that as described herein above with respect to reference number 1150.

At time index 2048, IV set 1124 is connected to first drug syringe 1126. For example, the connector of IV set 1124 associated with node identifier 143 is connected to a connector of first drug syringe 1126 associated with node identifier 164. Sensors of the tracking devices associated with node identifiers 143 and 164 are activated in response to the connection, which causes the tracking devices associated with node identifiers 143 and 164 to respectively transmit a signal including node identifier 143 associated with a physical parameter indicating an active state 1 of the node 143 and a signal including node identifier 164 associated with a physical parameter indicating an active state 1 of the node 164. Receiver 1104 receives the signals, determines that the signals were received within the sliding time window, e.g., within 2 seconds of each other, determines that a connection of node identifiers 143 and 164 is a permissible connection, (e.g., by consulting a look-up table of acceptable states and connections for node identifiers/devices), and updates the device register to include node identifier 143 associated with active state 1 and node identifier 164 associated with active state 1, and to include an indication that node 143 and node 164 are connected to one another, e.g., coincidence logic 143+164.

As shown by reference number 1154 in FIG. 11A, a medical device 1120 is disconnected from another medical device 1120 in connection area 1102. As an example, at time index 2051, IV set 1124 is disconnected from first drug syringe 1126. For example, the connector of IV set 1124 associated with node identifier 143 is disconnected from the connector of first drug syringe 1126 associated with node identifier 164. Sensors of the tracking devices associated with node identifiers 143 and 164 are activated in response to the disconnection, e.g., a pressure on pressure sensors of the tracking devices is removed because the devices are no longer connected, which causes the tracking devices associated with node identifiers 143 and 164 to respectively transmit a signal including node identifier 143 associated with a physical parameter indicating an inactive state 0 of the node 143 and a signal including node identifier 164 associated with a physical parameter indicating an inactive state 0 of the node 164. Receiver 1104 receives the signals, determines that the signals were received within the sliding time window, e.g., within 2 seconds of each other, determines that a disconnection of node identifiers 143 and 164 is a permissible disconnection, (e.g., by consulting a look-up table of acceptable states and connections for node identifiers/devices), and updates the device register to include node identifier 143 associated with inactive state 0 and node identifier 164 associated with inactive state 0, and to include an indication that node 143 and node 164 are now disconnected from one another, e.g., coincidence logic 143-164. In some non-limiting embodiments or aspects, if signals for node identifiers 143 and 163, which are stored as connected in the device register, are received that indicate different states, e.g., an activate state 1 for node identifier 143 and an inactive state 0 for node identifier 163, receiver 1104 determines an error condition and outputs an alert indicating that a detection or system error condition has occurred and/or that medical devices 1124 and/or 1126 are being misused.

As shown by reference number 1156 in FIG. 11A, a medical device 1120 leaves connection area 1102. For example, at time index 2052 in FIG. 11C, first drug syringe 1126 including node identifier 164 is in the connection area 1102, e.g., node identifier 164 is listed in the device register. At time index 2053, first drug syringe 1126 leaves connection area 1102. Receiver 1104 determines that node identifier 164 which is listed in the device register at time index 2052, is now outside connection area 1102 based on a lack of a response within a polling period from the tracking device associated with node identifier 164 to polling of connection area 1102. For example, receiver 1104 does not receive a signal including node identifier 164 in the polling period. Based on the lack of response, node identifier 164 is removed from the device register by the receiver 1104.

At time index 2055, second drug syringe 1128 including a tracking device associated with node identifier 193 enters the connection area 1102, and node identifier 193 is added to the device register in associated with inactive state 0, for example, in a manner similar to that as described herein above with respect to reference number 1150.

At time index 2058, flush syringe 1130 including a tracking device associated with node identifier 120 enters the connection area 1102, and node identifier 120 is added to the device register in associated with inactive state 0, for example, in a manner similar to that as described herein above with respect to reference number 1150.

At time index 2060, the connector of IV set 1124 associated with node identifier 143 is connected to the connector of flush syringe 1130 associated with node identifier 120. Sensors of the tracking devices associated with node identifiers 143 and 120 are activated in response to the connection, which causes the tracking devices associated with node identifiers 143 and 120 to respectively transmit a signal including node identifier 143 associated with a physical parameter indicating an active state 1 of the node 143 and a signal including node identifier 120 associated with a physical parameter indicating an active state 1 of the node 120. Receiver 1104 receives the signals, determines that the signals were received within the sliding time window, e.g., within 2 seconds of each other, determines that a connection of node identifiers 143 and 120 is a permissible connection, (e.g., by consulting a look-up table of acceptable states and connections for node identifiers/devices), and updates the device register to include node identifier 143 associated with active state 1 and node identifier 120 associated with active state 1, and to include an indication that node 143 and node 120 are connected to one another, e.g., coincidence logic 143+120.

At time index 2062, IV set 1124 is disconnected from flush syringe 1130. For example, the connector of IV set 1124 associated with node identifier 143 is disconnected from the connector of flush syringe 1130 associated with node identifier 120. Sensors of the tracking devices associated with node identifiers 143 and 120 are activated in response to the disconnection, which causes the tracking devices associated with node identifiers 143 and 120 to respectively transmit a signal including node identifier 143 associated with a physical parameter indicating an inactive state 0 of the node and a signal including node identifier 120 associated with a physical parameter indicating an active state 0 of the node. Receiver 1104 receives the signals, determines that the signals were received within the sliding time window, e.g., within 2 seconds of each other, determines that a disconnection of node identifiers 143 and 120 is a permissible disconnection, (e.g., by consulting a look-up table of acceptable states and connections for node identifiers/devices), and updates the device register to include node identifier 143 associated with inactive state 0 and node identifier 120 associated with inactive state 0, and to include an indication that node 143 and node 120 are now disconnected from one another, e.g., coincidence logic 143-120. In some non-limiting embodiments or aspects, if signals for node identifiers 143 and 163, which are stored as connected in the device register 143+120, are received that indicate different states, e.g., an activate state 1 for node identifier 143 and an inactive state 0 for node identifier 163, receiver 1104 determines an error condition and outputs an alert indicating that a detection or system error condition has occurred and/or that medical devices 1124 and/or 1130 are being misused.

At time index 2062, the device register includes information indicating a logical branch structure including predetermined device associations or connections, (e.g., between nodes/connectors 188 and 189 of catheter 1122 and between nodes/connectors 143 and 144 of IV set 1124 catheter, and/or detected device associations or connections, (e.g., between a node/connector 188 of catheter 1122 node/connector 144 of IV set 1124). Based on the logical branch structure, receiver 1104 can determine that catheter 1122 has a node 188 with a male Luer connector that is in fluid communication with a node 144 of IV set 1124, a male Luer connector, and that fluid entering node 143 of IV set 1124 flows through the connection of nodes 144 and 188 and exits node 189 of catheter 189. It is noted that with more complex IV sets with a greater number of connections/nodes, a branch structure is built using multiple nodes as multiple connection points as described in more detail herein below with respect to FIG. 12.

Figure 12:
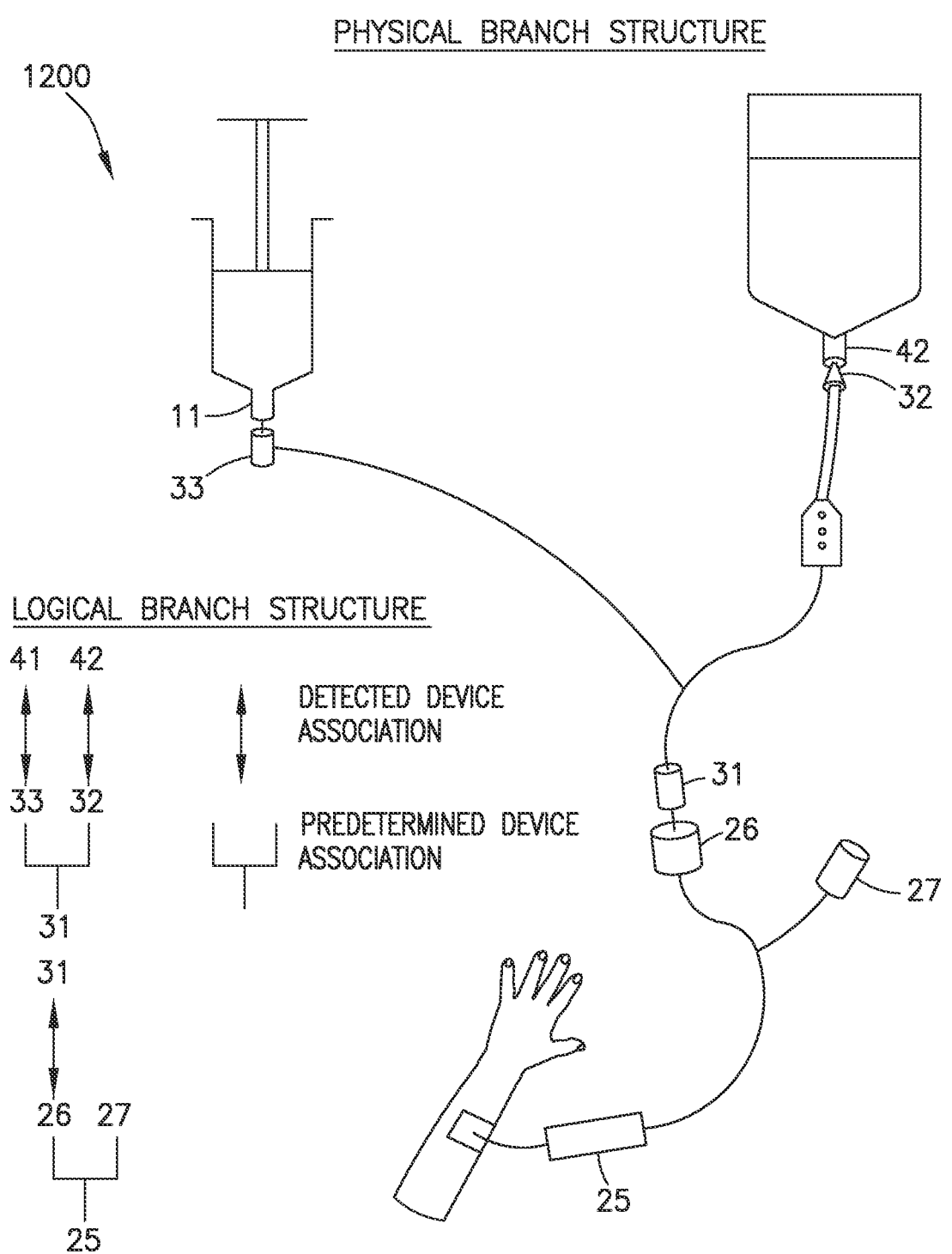
FIG. 12 is a diagram of an example physical device branch structure mapped to a computer-based logical device branch structure.

FIG. 12 is a diagram of an example physical device branch structure mapped to a computer-based logical device branch structure, e.g., as determined based on a device register database as described herein. Two digit node identifiers are used in the interest of brevity in implementation 1200; however, non-limiting embodiments or aspects can use node identifiers having any number of digits to indicate a precise product, indicate a branch structure of the precise product in a product database, and/or provide unique device identifiers for each precise product. As an example, the first digit in the node identifiers, e.g., the 10's place of the node identifier, indicates a device type. For example, device identifiers 20-29 are associated with catheters, device identifiers 30-39 are associated with IV sets, and device identifiers 40-49 are associated with syringes and IV bags. Nodes on these devices are indicated in second digit in the node identifiers, e.g., in the units place, and are unique for each device. In some non-limiting embodiments or aspects, node identifiers have sufficient digits to ensure that no two nodes have the same node identifier.

Although embodiments or aspects of the present disclosure have been described in detail for the purpose of illustration based on what is currently considered to be the most practical and preferred embodiments, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for identifying a physical connection state between a first device and a second device in a connection area, the system comprising at least one computing device including at least one processor, the at least one computing device programmed or configured to:
   receive, via wireless communication, a first plurality of physical parameter values of a first device from a first tracking device, provided on a tag or a carrier, that detects changes in physical state for the first device;
   receive, via wireless communication, a second plurality of physical parameter values of a second device from a second tracking device, provided on a tag or a carrier, that detects changes in physical state for the second device; and
   determine a physical connection state between the first device and the second device based on changes in the first plurality of physical parameter values and the second plurality of physical parameter values,
   wherein the first plurality of physical parameter values and the second plurality of physical parameter values are associated with a plurality of respective event times, wherein an event time indicates a time of a change in a physical state of the first device or the second device associated with the event time, and wherein the at least one computing device is programmed or configured to determine the physical connection state based on the plurality of event times.

2. The system of claim 1, wherein the at least one computing device is programmed or configured to control a flow of a fluid in a fluid flow path including the first device based on the physical connection state.

3. The system of claim 2, wherein the at least one computing device is programmed or configured to:
   receive a patient identifier associated with a patient;
   receive a medication identifier of a medication to be delivered to the patient via the fluid flow path;
   associate the patient identifier and the medication identifier with the first device of the fluid flow path; and
   control the flow of the fluid in the fluid flow path based on the patient identifier and the medication identifier.

4. The system of claim 1, wherein the at least one computing device is programmed or configured to:
   generate a digital representation of a fluid flow path including at least one device of the first device based on the physical connection state between the first device and the second device; and monitor a flow of a fluid in the fluid flow path based on the digital representation of the fluid flow path.

5. The system of claim 4, wherein the at least one computing device is programmed or configured to output or cause the output of human perceivable indication in the connection area, wherein the human perceivable indication indicates a status of the fluid flow path.

6. The system of claim 1, wherein the at least one computing device is programmed or configured to:

determine that the first device is within the connection area, the first device associated with a physical parameter value of the first plurality of physical parameter values;

receive a device identifier associated with the first device;

associate the device identifier with the physical parameter value of the first device; and update a device register including a list of devices in the connection area with the device identifier in association with the physical parameter value.

7. The system of claim 6, wherein the at least one computing device is programmed or configured to:

determine that the first device is outside the connection area; and remove the device identifier from the device register.

8. The system of claim 1, further comprising a data storage device including a compatibility table identifying which device identifiers and physical states are compatible for connection with another device identifier, and wherein the at least one computing device is programmed or configured to determine the physical connection state between the first device and the second device based on the compatibility table.

9. The system of claim 1, wherein at least one of: (i) the first physical parameter values or (ii) the second physical parameter values indicate a pressure or a light transmissivity of the first device or the second device, respectively.

10. The system of claim 1, wherein a physical parameter indicates a finite set of states of a physical state of the first device or the second device.

11. The system of claim 1, wherein a physical parameter indicates a magnitude of change in a physical state of the first device or the second device.

12. The system of claim 1, further comprising:

the first device and the second device;

a first sensor on the first device;

a second sensor on the second device, wherein the first sensor and the second sensor are configured to sense the physical states of the respective devices to determine the plurality of physical parameter values;

a first transmission source on the first device;

a second transmission source on the second device, wherein the first transmission source and the second transmission source are each configured to transmit the plurality of physical parameter values for the associated device; and a wireless signal receiver configured to:

detect the first transmission source and the second transmission source in the connection area, receive the first plurality of physical parameter values from the first transmission source, receive the second plurality of physical parameter values from the second transmission source, and provide the first and second plurality of physical parameter values to the at least one computing device including at least one processor.

13. The system of claim 12, wherein the wireless signal receiver comprises the at least one computing device including at least one processor.

14. The system of claim 13, wherein the at least one receiver comprises a plurality of receivers spaced apart from one another in the connection area.

15. The system of claim 14, wherein the remote computer is programmed or configured to:

receive a second plurality of physical parameter values of a second plurality of devices from a second plurality of transmission sources in a second connection area outside the first connection area, wherein the second plurality of physical parameters indicates physical states of the second plurality of devices; and determine at least one second physical connection state between the second plurality of devices based on the second plurality of physical parameters of the second plurality of devices.

16. The system of claim 1, wherein the at least one first devices comprises one of the following: a syringe, an IV spike, an IV access site, an IV bag, an IV set, a catheter, a medical device connector, or any combination thereof.

17. The system of claim 12, wherein the at least one first sensor comprises a pressure sensor.

18. The system of claim 12, further comprising:

at least one tag including the at least one first sensor and the at least one first transmission source are integrally formed with the at least one tag, wherein the at least one first sensor and the at least one first transmission source are sealed from an environment outside the at least one tag.

19. The system of claim 1, wherein the at least one first device forms at least a portion of a fluid flow path, and wherein the at least one tag is attached to the at least one first device at a fluid outlet or a fluid inlet of the at least one first device.

* * * * *